(12) United States Patent
Nash et al.

(10) Patent No.: US 7,192,576 B1
(45) Date of Patent: Mar. 20, 2007

(54) BIOLOGICALLY ACTIVE COMPLEX OF NR6 AND CARDIOTROPHIN-LIKE-CYTOKINE

(75) Inventors: Andrew Nash, Northcote (AU); Kim Maree Jachno, Altona (AU); Louis J. Fabri, Diamond Creek (AU); Kate Reid, Box Hill North (AU); Perry F. Bartlett, North Carlton (AU); Douglas J. Hilton, Warrandyte (AU); Yasuhiko Nakata, Ibaraki (JP); Masakazu Hasegawa, Ibaraki (JP)

(73) Assignee: Zenyth Operations Pty Ltd., Richmond (AU)

( * ) Notice: Subject to any disclaimer, the term of this patent is extended or adjusted under 35 U.S.C. 154(b) by 350 days.

(21) Appl. No.: 10/110,172

(22) PCT Filed: Oct. 6, 2000

(86) PCT No.: PCT/AU00/01216

§ 371 (c)(1),
(2), (4) Date: Aug. 26, 2002

(87) PCT Pub. No.: WO01/27157

PCT Pub. Date: Apr. 19, 2001

(30) Foreign Application Priority Data

Oct. 8, 1999 (AU) .................................... PQ3327
May 12, 2000 (AU) .................................... PQ7489

(51) Int. Cl.
C12N 15/19 (2006.01)
C12N 15/63 (2006.01)
A61K 38/19 (2006.01)
C07K 14/52 (2006.01)

(52) U.S. Cl. .................... 424/85.1; 530/351; 536/23.5; 536/24.3; 435/320.1

(58) Field of Classification Search .................... None
See application file for complete search history.

(56) References Cited

OTHER PUBLICATIONS

Mikayama et al. Proc. Natl. Acad. Sci. USA vol. 90, pp. 10056-10060, 1993.*
Voet et al. Biochemistry. John Wiley & Sons, Inc., pp. 126-128 and 228-234, 1990.*
Callard and Gearing (1994), The Cytokine Factsbook, Academic Press Ltd., pp. 39-40.*
J. Marmur et al., "Determination of the Base Composition of Deoxyribonucleic Acid from its Thermal Denaturation Temperature", *J. Mol. Biol.* 5:109-118 (1962).
W. M. Bonner et al., "A Film Detection Method for Tritium-Labelled Proteins and Nucleic Acids in Polyacrylamide Gels", *Eur. J. Biochem.* 46:83-88 (1974).
J. M. Chirgwin et al., "Isolation of Biologically Active Ribonucleic Acid from Sources Enriched in Ribonuclease", *Biochemistry* 18(24):5294-5299 (1979).

Ausubel et al., "Mapping by Partial Endonuclease Digestions", *Current Protocols in Molecular Biology* Suppl 9, Unit 3.3-3.32 (1987).
T. Taga et al., "Interleukin-6 Triggers the Association of its Receptor with a Possible Signal Transducer, gp130", *Cell* 58:573-581 (1989).
S. Mizushima et al., "pEF-BOS, a Powerful Mammalian Expression Vector", *Nucleic Acids Research* 18(17) (1990).
J.F. Bazan, "Structural Design and Molecular Evolution of a Cytokine Receptor Superfamily", *Proc. Natl. Acad. Sci. USA* 87:6934-6938 (1990).
S.R. Paul et al., "Molecular Cloning of a cDNA Encoding Interleukin 11, a Stromal Cell-Derived Lymphopoietic and Hematopoietic Cytokine", *Proc. Natl. Acad. Sci. USA* 87:7512-7516 (1990).
I. Kawashima et al., "Molecular Cloning of cDNA Encoding Adipogenesis Inhibitory Factor and Identity with Interleukin-11", *Febs Letters* 283(2):199-202 (1991).
D.P. Gearing et al., "Homology of the p40 Subunit of Natural Killer Cell Stimulatory Factor (NKSF) with the Extracellular Domain of the Interleukin-6 Receptor", *Cell* 66:9-10 (1991).
H. Baumann et al., "Interleukin-11 Regulates the Hepatic Expression of the Same Plasma Protein Genes as Interleukin-6", *The Journal of Biological Chemistry* 266(30):20424-20427 (1991).
M. Musashi et al., "Synergistic Interactions between Interleukin-11 and Interleukin-4 in Support of Proliferation of Primitive Hematopoietic Progenitors of Mice", *Blood* 78(6):1448-1451 (1991).
A.M. DeVos et al., "Human Growth Hormone and Extracellular Domain of its Receptor: Crystal Structure of the Complex", *Science* 255:306-312 (1992).
D.M. Merberg et al., "Sequence Similarity between NKSF and the IL-6/G-CSF Family", *Immunology Today* 13(2):77-78 (1992).
M.J. Layton et al., "A Major Binding Protein for Leukemia Inhibitory Factor in Normal Mouse Serum: Identification as a Soluble Form of the Cellular Receptor", *Proc. Natl. Acad. Sci. USA* 89:8616-8620 (1992).
K.R. Schibler et al., "Effect of Interleukin-11 on Cycling Status and Clonogenic Maturation of Fetal and Adult Hematopoietic Progenitors", *Blood* 80(4):900-903 (1992).

(Continued)

Primary Examiner—Prema Mertz
(74) Attorney, Agent, or Firm—Scully, Scott, Murphy & Presser, P.C.

(57) ABSTRACT

The present invention relates generally to a biologically active complex comprising at least two heterologous molecules. More particularly, the biologically active complex of the present invention comprises at least two polypeptides or parts, fragments, truncates or protease-activated forms of one or more of the polypeptides wherein the complex alone or in association with a receptor, ligand or other molecule facilitates proliferation, differentiation and/or survival of a cell. The identification of the biologically active complex of the present invention permits the assay for agonists and antagonists of the formation of the biologically active complex as well as therapeutic and diagnostic reagents based on the biologically active complex or interaction between the biologically active complex and a receptor, ligand or other molecule.

6 Claims, 9 Drawing Sheets

OTHER PUBLICATIONS

K. Tsuji et al., "Enhancement of Murine Hematopoiesis by Synergistic Interactions between Steel Factor (ligand for c-*kit*), Interleukin-11, and Other Early Acting Factors in Culture", *Blood* 79(*11*):2855-2860 (1992).

S.A. Burstein et al., "Leukemia Inhibitory Factor and Interleukin-11 Promote Maturation of Murine and Human Megakaryocytes In Vitro", *Journal of Cellular Physiology* 153:305-312 (1992).

Y-C Yang et al., "Interleukin-11 and its Receptor", *BioFactors* 4(*1*):15-21 (1992).

M. Teramura et al., "Interleukin-11 Enhances Human Megakaryocytopoiesis In Vitro", *Blood* 79(*2*):327-331 (1992).

Y. Yonemura et al., "Synergistic Effects of Interleukin 3 and Interleukin 11 on Murine Megakaryopoiesis in Serum-Free Culture", *Experimental Hematology* 20:1011-1016 (1992).

D.C. Keller et al., "Interleukin-11 Inhibits Adipogenesis and Stimulates Myelopoiesis in Human Long-Term Marrow Cultures", *Blood* 82(*5*):1428-1435 (1993).

G. Hangoc et al., "In Vivo Effects of Recombinant Interleukin-11 on Myelopoiesis in Mice", *Blood* 81(*4*):965-972 (1993).

X.X. Du et al., "Interleukin-11: A Multifunctional Growth Factor Derived from the Hematopoietic Microenvironment", *Blood* 83(*8*):2023-2030 (1994).

Y. Hirata et al., "ADP Ribosyl Cyclase Activity of a Novel Bone Marrow Stromal Cell Surface Molecule, BST-1", *Febs Letter* 356:244-248 (1994).

N.C. Wrighton et al., "Small Peptides as Potent Mimetics of the Protein Hormone Erythropoietin", *Science* 273:458-463 (1996).

D.J. Hilton et al., "Cloning and Characterization of a Binding Subunit of the Interleukin 13 Receptor that is also a Component of the Interleukin 4 Receptor", *Proc. Natl. Acad. Sci. USA* 93:497-501 (1996).

S.F. Altschul et al., "Gapped BLAST and PSI-BLAST: a New Generation of Protein Database Search Programs", *Nucleic Acids Research* 25(*17*):3389-3402 (1997).

S.E. Cwirla et al., "Peptide Agonist of the Thrombopoietin Receptor as Potent as the Natural Cytokine", *Science* 276:1696-1699 (1997).

Y. Shi et al., "Computational EST Database Analysis Identifies a Novel Member of Neuropoietic Cytokine Family", *Biochemical and Biophysical Research Communications* 262(*1*):132-138 (1999).

Greg C. A. Elson, et al., "CLF associates with CLC to form a functional heteromeric ligand for the CNTF receptor complex", *Nature Neuroscience*, 3(9): 867-872 (2000).

\* cited by examiner

Determined N-terminal amino acid sequence

LxRTGDPGPGPSI

NH₂-terminal sequence analysis

Sequence 1  ASISARQDYKDDDD    Expected expressed NR6 seq

7:1 sequence ratio (NR6:CLC)

X denotes glycosylation

Sequence 2  LXRTGDPGPSIQK    Expected expressed CLC seq

Figure 4

BIOLOGICALLY ACTIVE COMPLEX OF NR6 AND CARDIOTROPHIN-LIKE-CYTOKINE

FIELD OF THE INVENTION

The present invention relates generally to a biologically active complex comprising at least two heterologous molecules. More particularly, the biologically active complex of the present invention comprises at least two polypeptides or parts, fragments, truncates or protease-activated forms of one or more of the polypeptides wherein the complex alone or in association with a receptor, ligand or other molecule facilitates proliferation, differentiation and/or survival of a cell. The identification of the biologically active complex of the present invention permits the assay for agonists and antagonists of the formation of the biologically active complex as well as therapeutic and diagnostic reagents based on the biologically active complex or interaction between the biologically active complex and a receptor, ligand or other molecule.

BACKGROUND OF THE INVENTION

Bibliographic details of the publications numerically referred to in this specification are collected at the end of the description.

Reference to any prior art in this specification is not, and should not be taken as, an acknowledgment or any form of suggestion that this prior art forms part of the common general knowledge in Australia or any other country.

The rapidly increasing sophistication of recombinant DNA techniques is greatly facilitating research into the medical and allied health fields. Cytokine research is of particular importance, especially as these molecules regulate the proliferation, differentiation and function of a wide variety of cells. Administration of recombinant cytokines or regulating cytokine function and/or synthesis is becoming increasingly the focus of medical research into the treatment of a range of disease conditions.

Despite the discovery of a range of cytokines and other secreted regulators of cell function, comparatively few cytokines are directly used or targeted in therapeutic regimens. One reason for this is the pleiotropic nature of many cytokines. For example, interleukin (IL)-11 is a functionally pleiotropic molecule (1,2), initially characterized by its ability to stimulate proliferation of the IL-6-dependent plasmacytoma cell line, T11 65 (3). Other biological actions of IL-11 include induction of multipotential haemopoietin progenitor cell proliferation (4,5,6), enhancement of megakaryocyte and platelet formation (7,8,9,10), stimulation of acute phase protein synthesis (11) and inhibition of adipocyte lipoprotein lipase activity (12,13).

Other important cytokines in the IL-11 group include IL-6, leukaemia inhibitory factor (LIF), oncostatin M (OSM), ciliary neurotrophic factor (CNTF) and cardiotrophin-1 (CT-1). All these cytokines exhibit pleiotropic properties with significant activities in proliferation, differentiation and survival of cells. Members of the haemopoietin receptor family are defined by the presence of a conserved amino acid domain in their extracellular region. However, despite the low level of amino acid sequence conservation between other haemopoietin receptor domains of different receptors, they are all predicted to assume a similar tertiary structure, centred around two fibronectin-type III repeats (18,19).

Recently a molecule has been identified which has cardiotrophin-like properties (26). This molecule has been referred to as cardiotrophin-like cytokine (CLC) and novel neurotrophic factor 1(NNT-1) [U.S. Pat. No. 5,741,772].

Cytokines signal through cell-associated receptors. These receptors are classified into families based on sequence and structural similarities.

The size of the haemopoietin receptor family has now become extensive and includes the cell surface receptors for may cytokines including interleukin-2 (IL-2), IL-3, IL-4, IL-5, IL-6, IL-7, IL-9, IL-11, IL-12, IL-13, IL-15, granulocyte colony stimulating factor (G-CSF), granulocyte-macrophage-CSF (GM-CSF), erythropoietin, thrombopoietin, leptin, LIF, OSM, CNTF, CT-1, growth hormone and prolactin. Although most of the members of the haemopoietin receptor family act as classic cell surface receptors, binding their cognate ligand at the cell surface and initiating intracellular signal transduction, some receptors are also produced in naturally occurring soluble forms. These soluble receptors can either act as cytokine antagonists, by binding to cytokines and inhibiting productive interactions with cell surface receptors (e.g. LIF binding protein, (20) or as agonists, binding to cytokine and potentiating interaction with cell surface receptor components (e.g. soluble interleukin-6 receptor a-chain; (21)). Still other members of the family appear to be produced only as secreted proteins, with no evidence of a cell surface form. In this regard, the IL-12 p40 subunit is a useful example. The cytokine IL-12 is secreted as a heterodimer composed of a p35 subunit which shows similarity to cytokines such as IL-6 (22) and a p40 subunit which shares similarity with the IL-6 receptor a-chain (23). In this case the soluble receptor acts as part of the cytokine itself and essential to formation of an active protein. In addition to acting as cytokines (e.g. IL-12p40), cytokine agonists (e.g. IL-6 receptor a-chain) or cytokine antagonists (LIF binding protein), members of the haemopoietin receptor have been useful in the discovery of small molecule cytokine mimetics. For example, the discovery of peptide mimetics of two commercially valuable cytokines, erythropoietin and thrombopoietin, centred on the selection of peptides capable of binding to soluble versions of the erythropoietin and thrombopoietin receptors (24,25).

Due to the importance and multifactorial nature of these cytokines, there is a need to further investigate and elucidate the molecular interactions not only between cytokines and their receptors but also between cytokines themselves.

SUMMARY OF THE INVENTION

Nucleotide and amino acid sequences are referred to by a sequence identifier, i.e. <400>1, <400>2, etc. A sequence listing is provided before the Examples.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention is directed to a biologically active complex comprising at least two heterologous molecules which complex alone or in association with a receptor, ligand or other molecule facilitates proliferation, differentiation and/or survival of a cell.

Another aspect of the present invention provides a biologically active complex comprising at least two polypeptides or parts, fragments, truncates or protease-activated forms of one or more of the polypeptides which complex alone or in association with a receptor, ligand or other molecule facilitates proliferation, differentiation and/or survival of a cell.

Still another aspect of the present invention provides a biologically active complex comprising at least two polypeptides or parts, fragments, truncates or protease-activated forms of one or more of the polypeptides wherein at least one of said polypeptides is NR6 or a part, fragment, truncate or protease-activated form thereof and wherein said complex alone or in association with a receptor, ligand or other molecule facilitates proliferation, differentiation and/or survival of a cell.

Yet another aspect of the present invention is directed to a biologically-active complex comprising the structure:—

$$[X^1]_n(a) [X_2]_{n1}(b)[X_3]_{n2} \ldots [X_d]_{n3}$$

wherein $X_1$ and $X_2$ are different and one is NR6 and the other is CLC or parts, fragments, truncates or protease-activated forms thereof;

$X_3 \ldots X_d$ are optionally present represent other members of the complex such as a cytokine or cytokine-like molecule;

n and $n_1$ may be the same or different and each is from about 1 to about 50;

$n_2$ and $n_3$ may be the same or different and each is from 0 to about 50;

(a) and (b) may be the same or different and represent the bonds, interactions or other "forces" which keep the members together in the complex.

Even yet another aspect of the present invention provides a biologically active complex comprising the structure:—

$$[X^1]_{a3}[NR6]_a[CLC]_{a1}[NR6]_{a2}[X^1]_{a4}$$

wherein:

$X^1$ is optionally present and is a cytokine or cytokine-like molecule;

a is from about 0 to 10;

$a_1$ is from 1 to about 10;

$a_2$ is from 0 to 10;

with the proviso that if one of a or $a_2$ is 0 then the other of a or $a_2$ cannot be 0;

$a_3$ is from about 0 to 10;

$a_4$ is from about 0 to 10;

with the proviso that if $X^1$ is present then either $a_3$ or $a_4$ is 0.

Another aspect of the present invention provides a genetic construct comprising a sequence of nucleotides substantially as set forth in <400>1 or a nucleotide sequence having at least 60% similarity to the nucleotide sequence set forth in <400>1 or a nucleotide sequence capable of hybridizing thereto under low stringency conditions at 42° C. and a sequence of nucleotides encoding CLC or a modified form thereof.

Still another aspect of the present invention provides a genetic construct comprising a sequence of nucleotides substantially as set forth in <400>3 or a nucleotide sequence having at least 60% similarity to the nucleotide sequence set forth in <400>3 or a nucleotide sequence capable of hybridizing thereto under low stringency conditions at 42° C. and a sequence of nucleotides encoding CLC or a modified form thereof.

Yet another aspect of the present invention provides a genetic construct comprising a sequence of nucleotides substantially as set forth in <400>5 or a nucleotide sequence having at least 60% similarity to the nucleotide sequence set forth in <400>5 or a nucleotide sequence capable of hybridizing thereto under low stringency conditions at 42° C. and a sequence of nucleotides encoding CLC or a modified form thereof.

Even yet another aspect of the present invention provides a genetic construct comprising a sequence of nucleotides substantially as set forth in <400>7 or a nucleotide sequence having at least 60% similarity to the nucleotide sequence set forth in <400>7 or a nucleotide sequence capable of hybridizing thereto under low stringency conditions at 42° C. and a sequence of nucleotides encoding CLC or a modified form thereof.

Another aspect of the present invention provides a genetic construct comprising a sequence of nucleotides substantially as set forth in <400>9 or a nucleotide sequence having at least 60% similarity to the nucleotide sequence set forth in <400>9 or a nucleotide sequence capable of hybridizing thereto under low stringency conditions at 42° C. and a sequence of nucleotides encoding CLC or a modified form thereof.

Still another aspect of the present invention is directed to a genetic construct substantially as set forth in <400>11 or a nucleotide sequence having at least 60% similarity to the nucleotide sequence set forth in <400>11 or a nucleotide sequence capable of hybridizing thereto under low stringency conditions at 42° C. and a sequence of nucleotides encoding CLC or a modified form thereof.

Yet another aspect of the present invention provides a genetic construct comprising a sequence of nucleotides substantially set forth in <400>12 or a nucleotide sequence having at least 60% similarity to the nucleotide sequence set forth in <400>12 or a nucleotide sequence capable of hybridizing thereto under low stringency conditions at 42° C. and a sequence of nucleotides encoding CLC or a modified form thereof.

Even yet another aspect of the present invention provides a genetic construct comprising a sequence of nucleotides substantially set forth in <400>13 or a nucleotide sequence having at least 60% similarity to the nucleotide sequence set forth in <400>13 or a nucleotide sequence capable of hybridizing thereto under low stringency conditions at 42° C. and a sequence of nucleotides encoding CLC or a modified form thereof.

Another aspect of the present invention provides an expression vector comprising a nucleic acid molecule encoding NR6 and CLC or modified forms thereof said expression vector capable of expression in a selected host cell.

Still another aspect of the present invention provides a genetic construct comprising a sequence of nucleotides encoding NR6 or a derivative thereof having an amino acid sequence as set forth in <400>2 or having at least about 50% similarity to all or part thereof, said genetic construct further comprising a sequence of nucleotides encoding CLC or a modified form thereof.

Yet another aspect of the present invention provides a genetic construct comprising a sequence of nucleotides encoding NR6 or a derivative thereof having an amino acid sequence as set forth in <400>4 or having at least about 50% similarity to all or part thereof, said genetic construct further comprising a sequence of nucleotides encoding CLC or a modified form thereof.

Even still another aspect of the present invention provides a genetic construct comprising a sequence of nucleotides encoding NR6 or a derivative thereof having an amino acid sequence as set forth in <400>6 or having at least about 50% similarity to all or part thereof, said genetic construct further comprising a sequence of nucleotides encoding CLC or a modified form thereof.

Another aspect of the present invention provides a genetic construct comprising a sequence of nucleotides encoding NR6 or a derivative thereof having an amino acid sequence as set forth in <400>8 or having at least about 50% similarity to all or part thereof, said genetic construct further comprising a sequence of nucleotides encoding CLC or a modified form thereof.

Still another aspect of the present invention provides a genetic construct comprising a sequence of nucleotides encoding NR6 or a derivative thereof having an amino acid sequence as set forth in <400>14 or having at least about 50% similarity to all or part thereof, said genetic construct further comprising a sequence of nucleotides encoding CLC or a modified form thereof.

Yet another aspect of the present invention provides a genetic construct comprising a sequence of nucleotides encoding NR6 or a derivative thereof having an amino acid sequence as set forth in one or more of <400>15 or having at least about 50% similarity to all or part thereof, said genetic construct further comprising a sequence of nucleotides encoding CLC or a modified form thereof.

Another aspect of the present invention contemplates a method of modulating activity of the complex as hereinbefore described, said method comprising administering to a subject a modulating effective amount of a molecule for a time and under conditions sufficient to increase or decrease the biological activity of the complex.

Still another aspect of the present invention is directed to antibodies to the complex and its derivatives.

Yet another aspect of the present invention contemplates a method for detecting the complex as hereinbefore described in a biological sample from a subject, said method comprising contacting said biological sample with an antibody specific for the complex (or a component thereof) or its derivatives or homologues for a time and under conditions sufficient for an antibody complex to form, and then detecting said antibody.

Even yet another further aspect of the present invention contemplates the use of the biologically active complex or its functional derivatives in the manufacture of a medicament for the treatment of conditions resulting from aberrations in the complex or in reduced or excessive amounts of the complex.

Another aspect of the present invention contemplates a ligand or receptor for the complex such as in isolated or recombinant form, or a derivative of said ligand or receptor.

Still another aspect of the present invention further contemplates knockout animals such as mice or other murine species for components of the complex gene including homozygous and heterozygous knockout animals.

Even still another aspect of the present invention contemplates a method of identifying an agent capable of modulating the effects of a biologically active complex as herein defined, said method comprising screening for agents which are capable of interacting with the complex or interfering or otherwise antagonizing or promoting or otherwise agonizing interaction between the heterologous molecules of said complex.

The complex and its components and in particular CLC, NR6 and/or a CLC-NR6 complex are particularly useful in inducing neurotrophic activity.

Conditioned medium was collected from CHO cells following transfection with either FLAG-NR6 or HA-CLC, or FLAG-NR6 and HA-CLC together. The conditioned media was immunoprecipitated with either anti-haemagglutinin (HA) antibody-sepharose (panel A and B), or anti-FLAG (M2) antibody-agarose (panel C and D). All samples were electrophoresed under reducing conditions except for samples in lanes 1 and 2 of panel C and D (*). Following electrophoretic transfer to PVDF, membranes were probed with anti-FLAG antibody (panel A) and anti-HA antibody (panel C). These membranes were subsequently stripped (incompletely) and reprobed with the antibody used for immunoprecipitation (panel B and D).

FIG. 2 is an amino acid sequence analysis of the 27–29 kD protein that co-purifies with FLAG-NR6.

SDS-PAGE analysis of proteins purified from conditioned media by anti-FLAG affinity chromatography (panel A). The 27–29 kD band was transferred to PVDF and excised for $NH_2$-terminal amino acid sequencing. The determined sequence of the 27–29 kD band is shown in panel B. This sequence is identical to mature human CLC.

FIG. 3 is a representation showing size exclusion fractionation of FLAG-NR6—CLC complexes. FLAG-NR6—CLC purified by anti-FLAG M2 affinity chromatography was subjected to size exclusion chromatography using a Pharmacia Superose 12 10/30 column at a flow rate of 1 ml/min. (A) The elution profile (OD 215 nm) of FLAG-NR6—CLC is compared with that of purified FLAG-NR6 alone. Elution time for three molecular weight, standards (BSA dimer, BSA monomer, trypsin inhibitor) is shown. (B) Non-reducing SDS-PAGE analysis of fractions collected at 0.5 minute intervals. Aliquots collected from each fraction were concentrated and analyzed by SDS-PAGE, non reducing conditions, 4–20% w/v gradient gel. Proteins were visualised by Coomassie blue staining.

FIG. 4 is a diagrammatical representation of a $NH_2$-terminal sequence analysis of pooled fractions from size exclusion chromatography. Two distinct sequences were identified corresponding to FLAG-NR-6 and CLC. The ratio at which the two sequences were detected (7:1, NR6:CLC) correlates well with staining intensity on the SDS-PAGE and like the SDS-PAGE also suggests that more NR6 is expressed than CLC.

Figure 5:
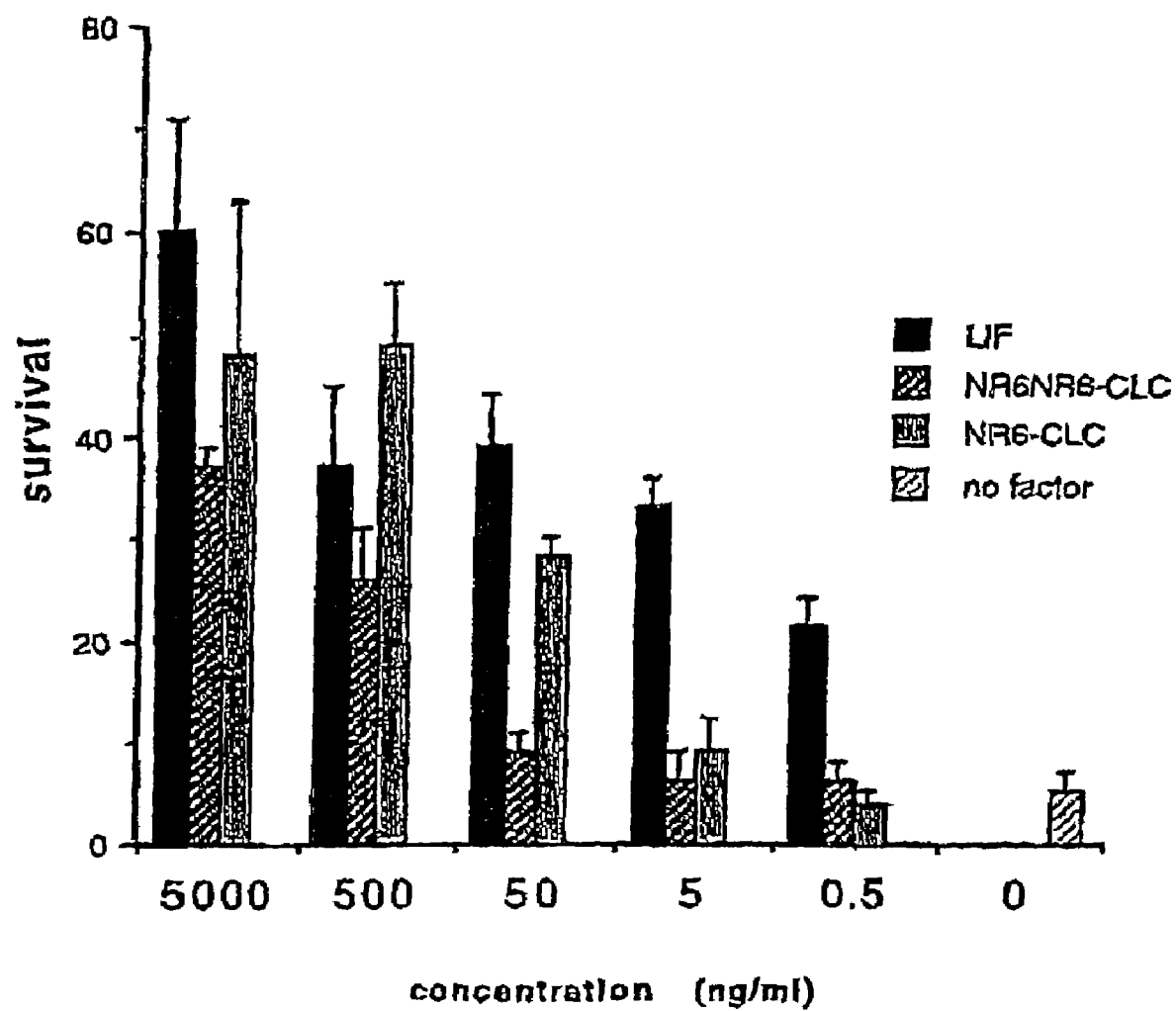

FIG. 5 is a graphical representation showing analysis of neurotrophic activity of CLC co-expressed with NR6. Dorsal root ganglia were dissected from newborn C57/BL mice and dissociated to form a single cell suspension. Cells were plated in HLA plates which had been pre-treated with polyornithine and laminin, in Monomed media with 1% w/v FBS and cytokines as indicated. Forty-eight hrs later the number of surviving neurons was counted. Leukaemia inhibitory factor (LIF), a growth factor with known potent neurotrophic activity, was included as a positive control. Each bar represents the mean of three wells and the error bars are standard deviations.

Table 1 is a list of single and three letter abbreviations used throughout the specification.

Table 2 is a summary of amino acid and nucleotide sequence identifiers.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

TABLE 2

| SEQUENCE IDENTIFIER | DESCRIPTION |
|---|---|
| <400>1 | Nucleotide sequence of NR6.1[1] |
| <400>2 | Amino acid sequence of NR6.1 |
| <400>3 | Nucleotide sequence of NR6.2[2] |
| <400>4 | Amino acid sequence of NR6.2 |
| <400>5 | Nucleotide sequence of NR6.3[3] |
| <400>6 | Amino acid sequence of NR6.3 |
| <400>7 | Nucleotide sequence of products generated by 5' RACE of brain cDNA using NR6 specific primers[4] |
| <400>8 | Amino acid sequence of <400>7 |
| <400>9 | Nucleotide sequence of clone HFK-66 encoding human NR6 |
| <400>10 | Amino acid sequence of <400>9 |
| <400>11 | Genomic nucleotide sequence of murine NR6 |
| <400>12 | Genomic nucleotide sequence of murine NR6 containing additional 5' sequence |
| <400>13 | Nucleotide sequence of NR6 |
| <400>14 | Amino acid sequence of <400>13 |
| <400>15 | Amino acid sequence of <400>11 |
| <400>16 | Amino acid sequence of NR6 |
| <400>17 | Nucleotide sequence unique to 5' RACE of brain cDNA |
| <400>18 | Amino acid sequence for <400>17 |
| <400>19 | Nueleotide sequence of CLC |
| <400>20 | Amino acid sequence of CLC |
| <400>21 | Sense primer |
| <400>22 | Anti-sense primer |
| <400>23 | HA epitope tag |
| <400>24 | IL-3 signal sequence |
| <400>25 | Sense primer |
| <400>26 | Anti-sense primer |
| <400>28 | Artificial peptide |
| <400>29 | Artificial peptide |
| <400>30 | Artificial peptide |
| <400>31 | Artificial peptide |

[1]The polyadenylation signal AATAAATAAA is at nucleotide position 1451 to 1460; NR6.1 (<400>1) and NR6.2 (<400>3) are identical to nucleotide 1223 encoding Q407, the represents the end of an exon. NR6.1 splices out an exon present only in NR6.2 and uses a different reading frame for the final exon which is shared with NR6.2; this corresponds to amino acids VLPAKL at amino acid residue positions 408–413. The region of 3'-untranslatedDNA shared by NR6.1, NR6.2 and NR6.3 is from nucleotide 1240 to 1475. The WSXWS motif is at amino acid residues 330 to 334.

[2]The polyadenylation signal AATAAA is at nucleotide positions 1494 to 1503. The WSXWS motif is at amino acid residues 330 to 334. NR6.1 and NR6.2 are identical to nucleotide 1223 encoding Q407 which represents the end of an exon. NR6.2 splices in an exon beginning at amino acid residue D408, nucleotide 1224 and ends at residue G422, nucleotide 1264. The region of 3'-untranslated DNA shared by NR6.1, NR6.2 and NR6.3 is from nucleotide position 1283 to 1517.

[3]The polyadenylation signal AATAAA is at nucleotide positions 1494 to 1503. The WSXWS motif is at amino acid residues 330 to 334. NR6.1 and NR6.2 are identical to nucleotide 1223 encoding Q407 which represents the end of an exon. NR6.2 splices in an exon beginning at amino acid residue D408, nucleotide 1224 and ends at residue G422, nucleotide 1264. The region of 3'-untranslated DNA shared by NR6.1, NR6.2 and NR6.3 is from nucleotide position 1283 to 1517.

[4]The nucleotide sequence is identical to NR6.1, NR6.2 and NR6.3 from nucleotide C151, the first nucleotide for Pro51. The numbering from this nucleotide is the same as for <400>3 and <400>5. The 5 of this point is unique to the products generated by 5' RACE not being found in NR6.1, NR6.2 and NR6.3 and is represented in <400>16 and <400>17.

DETAILED DESCRIPTION OF THE PREFERRED EMBODIMENTS

In work leading up to the present invention, the inventors identified an interaction between a haemopoietin receptor and a cytokine or cytokine-like molecule resulting in a biologically active complex.

The identification of this biologically active complex permits the rational design of agonist and antagonists of the interaction as well as interaction between the biologically active complex and other receptors, cytokines or cytokine-like molecules or other molecules. The biologically active complex itself may also be used in the development of therapeutics and diagnostics.

In one embodiment, the complex and/or its components have neurotrophic activity.

One aspect of the present invention is directed to a biologically active complex comprising at least two heterologous molecules which complex alone or in association with a receptor, ligand or other molecule facilitates proliferation, differentiation and/or survival of a cell.

Reference herein to "heterologous" means inter alia that two molecules differ in physical structure, biological activity or origin. For example, when the molecules are polypeptides, they are either encoded by different genes or represent, for example, splice variants of mRNA from the one gene. Preferably, the heterologous molecules differ at the amino acid level, after optimal alignment, by at least 5%.

Reference to a "complex" and in particular a "biologically active complex" means an association or other form of interaction between at least two molecules. The molecules may form a complex by a variety of mechanisms including covalent bonds, disulphide bridges, van der waals forces, ionic latticing, hydrogen bonds, amide bonds or physically being held together as a consequence of mutual folding.

In a particularly preferred embodiment, the at least two molecules in the complex are peptides, polypeptides or proteins.

Accordingly, another aspect of the present invention provides a biologically active complex comprising at least two polypeptides or parts, fragments, truncates or protease-activated forms of one or more of the polypeptides which complex alone or in association with a receptor, ligand or other molecule facilitates proliferation, differentiation and/ or survival of a cell.

Preferably, the at least two polypeptides are heterologous with respect to each other meaning, as stated above, that both polypeptides are encoded by different genes or are, for example, splice variants from a single gene.

Parts and fragments of a polypeptide include peptides. A "protease-activated polypeptide" is a polypeptide where some portion has been enzymatically cleaved or processed. For example, an N-terminal or C-terminal amino acid sequence may be cleaved off by the protease. Reference herein to a "protease" means a protease in its most general sense and includes any enzyme which cleaves an amino acid chain at a defined location or at a defined sequence and includes a peptidase and a proteinase.

In a particularly preferred embodiment, at least one polypeptide in the complex is a soluble receptor and more particularly a soluble haemopoietin receptor. In a most preferred embodiment, the receptor is referred to as "NR6" which is described in International Patent Publication Number WO 98/11225.

Accordingly, another aspect of the present invention provides a biologically active complex comprising at least two polypeptides or parts, fragments, truncates or protease-activated forms of one or more of the polypeptides wherein at least one of said polypeptides is NR6 or a part, fragment, truncate or protease-activated form thereof and wherein said complex alone or in association with a receptor, ligand or other molecule facilitates proliferation, differentiation and/or survival of a cell.

Another polypeptide in the complex is preferably a cytokine or cytokine-like molecule.

According to this embodiment, the present invention contemplates a biologically active complex comprising at least two polypeptides or parts, fragments, truncates or protease-activated forms of the polypeptides wherein at least one polypeptide is NR6 and at least one other polypeptide is a cytokine or cytokine-like molecule or a part, fragment, truncate or protease-activated form of NR6 and/or the cytokine or cytokine-like molecule and wherein said complex alone or in association with a receptor, ligand or other molecule facilitates proliferation, differentiation and/or survival of a cell.

In a particularly preferred embodiment, at least one of the polypeptides is cardiotrophin-like cytokine (CLC). Accordingly, a particularly preferred biologically active complex comprises at least NR6 and CLC or parts, fragments, truncates or protease-activated forms of NR6 and/or CLC.

The biologically active complex identified in accordance with the present invention may comprise two molecules and in particular two peptides or may comprise more than two molecules. Additional members of the complex include receptors, ligands, cytokines and cytokine-like molecules. For example, the complex may include gp130 or a cytokine and gp130.

Accordingly, another aspect of the present invention is directed to a biologically-active complex comprising the structure:—

$$[X_1]_n(a)[X_2]_{n1}(b)[X_3]_{n2} \ldots [X_d]_{n3}$$

wherein $X_1$ and $X_2$ are different and one is NR6 and the other is CLC or parts, fragments, truncates or protease-activated forms thereof;

$X_3 \ldots X_d$ are optionally present represent other members of the complex such as a cytokine or cytokine-like molecule;

n and $n_1$ may be the same or different and each is from about 1 to about 50;

$n_2$ and $n_3$ may be the same or different and each is from 0 to about 50;

(a) and (b) may be the same or different and represent the bonds, interactions or other "forces" which keep the members together in the complex.

According to this embodiment, at least the NR6 and/or CLC may be in multiple form. Furthermore, $X_1$, $X_2$, $X_3 \ldots X_d$ may be in any order. Preferred values for n and $n_1$ are from about 1 to about 5.

In a particularly preferred embodiment, $X_3$ is CNTFR, gp130, LIFR or other receptor molecule or cytokine-like molecule.

Accordingly, another aspect of the present invention provides a biologically active complex comprising the structure:—

$$[X^1]_{a3}[NR6]_a[CLC]_{a1}[NR6]_{a2}[X^1]_{a4}$$

wherein $X^1$ is optionally present and is a cytokine or cytokine-like molecule;

a is from about 0 to 10;

$a_1$ is from 1 to about 10;

$a_2$ is from 0 to 10;

with the proviso that if one of a or $a_2$ is 0 then the other of a or $a_2$ cannot be 0;

$a_3$ is from about 0 to 10;

$a_4$ is from about 0 to 10;

with the proviso that if $X^1$ is present then either $a_3$ or $a_4$ is 0.

Reference herein to NR6 and CLC means a molecule from any animal or avian species such as from humans, primates, laboratory test animals (e.g. mice, rats, rabbits, guinea pigs), companion animals (e.g. cats, dogs), captive wild animals, poultry birds, game birds, caged birds, reptiles or fish.

Preferably, the NR6 and/or CLC is of human, primate or murine origin.

Nucleotide sequences encoding NR6 are disclosed in WO 98/11225. The nucleotide sequence encoding CLC is represented in Genbank AR002595, AC005849 and AF172854 (see also U.S. Pat. No. 5,741,772 and International Patent Publication No. WO 99/00415).

The present invention preferably provides the biologically active complex in isolated form such that it has undergone at least one purification or co-precipitation step from culture medium or biological fluid. Reference herein to "biologically active" means that the complex has a direct effect on a cell or biochemical pathway or physiological process or has this effect after processing or interaction with receptor, ligand or other molecule.

The present invention further comprises genetic constructs comprising a first nucleotide sequence encoding one or other of NR6 or CLC or modified forms thereof, and a second nucleotide sequence encoding the other of NR6 or CLC. The genetic construct may also comprise other nucleotide sequences encoding further members of the complex. Preferably, each nucleotide sequence encoding NR6 and CLC is operably linked to the same or a separate promoter sequence. The genetic construct according to this aspect of the present invention is conveniently used to co-express nucleotide sequences encoding NR6 and CLC. Alternatively, separate genetic constructs each encoding one or other of NR6 and CLC are used to transfect a cell for co-expression.

Reference herein to "NR6" and "CLC" or other modified forms includes reference to parts, fragments and truncates thereof. These terms also include various splice forms of NR6 and CLC.

The present invention further provides a genetic construct comprising a sequence of nucleotides substantially as set forth in <400>1 or a nucleotide sequence having at least 60% similarity to the nucleotide sequence set forth in <400>1 or a nucleotide sequence capable of hybridizing thereto under low stringency conditions at 42° C. and a sequence of nucleotides encoding CLC or a modified form thereof.

In a related embodiment, the present invention provides a genetic construct comprising a sequence of nucleotides substantially as set forth in <400>3 or a nucleotide sequence having at least 60% similarity to the nucleotide sequence set forth in <400>3 or a nucleotide sequence capable of hybridizing thereto under low stringency conditions at 42° C. and a sequence of nucleotides encoding CLC or a modified form thereof.

In another related embodiment, the present invention provides a genetic construct comprising a sequence of nucleotides substantially as set forth in <400>5 or a nucleotide sequence having at least 60% similarity to the nucleotide sequence set forth in <400>5 or a nucleotide sequence capable of hybridizing thereto under low stringency conditions at 42° C. and a sequence of nucleotides encoding CLC or a modified form thereof.

In a further related embodiment, the present invention provides a genetic construct comprising a sequence of nucleotides substantially as set forth in <400>7 or a nucleotide sequence having at least 60% similarity to the nucleotide sequence set forth in <400>7 or a nucleotide sequence capable of hybridizing thereto under low stringency conditions at 42° C. and a sequence of nucleotides encoding CLC or a modified form thereof.

In yet a further related embodiment, the present invention provides a genetic construct comprising a sequence of nucleotides substantially as set forth in <400>9 or a nucleotide sequence having at least 60% similarity to the nucleotide sequence set forth in <400>9 or a nucleotide sequence capable of hybridizing thereto under low stringency conditions at 42° C. and a sequence of nucleotides encoding CLC or a modified form thereof.

Still yet a further embodiment of the present invention is directed to a genetic construct substantially as set forth in <400>11 or a nucleotide sequence having at least 60% similarity to the nucleotide sequence set forth in <400>11 or a nucleotide sequence capable of hybridizing thereto under low stringency conditions at 42° C. and a sequence of nucleotides encoding CLC or a modified form thereof.

In still yet another embodiment, the present invention provides a genetic construct comprising a sequence of nucleotides substantially set forth in <400>12 or a nucleotide sequence having at least 60% similarity to the nucleotide sequence set forth in <400>12 or a nucleotide sequence capable of hybridizing thereto under low stringency conditions at 42° C. and a sequence of nucleotides encoding CLC or a modified form thereof.

Another embodiment of the present invention provides a genetic construct comprising a sequence of nucleotides substantially set forth in <400>13 or a nucleotide sequence having at least 60% similarity to the nucleotide sequence set forth in <400>13 or a nucleotide sequence capable of hybridizing thereto under low stringency conditions at 42° C. and a sequence of nucleotides encoding CLC or a modified form thereof.

Reference to CLC or a modified form includes a molecule having an amino acid sequence set forth in <400>20 or having an amino acid sequence of at least 60% similarity thereto or encoded by a nucleotide sequence substantially as set forth in <400>19 or having at least 60% similarity thereto or a sequence capable of hybridizing thereto under low stringency conditions at 42° C.

The term "receptor" is used in its broadest sense and includes any molecule capable of binding, associating or otherwise interacting with a ligand. Generally, the interaction will have a signalling effect although the present invention is not necessarily so limited. For example, the "receptor" may be in soluble form, often referred to as a cytokine binding protein. A receptor may be deemed a receptor notwithstanding that its ligand or ligands has or have not been identified.

Different forms of NR6 are referred to as, for example, NR6.1, NR6.2 and NR6.3. The nucleotide and corresponding amino acid sequences for these molecules are represented in <400>1, <400>3 and <400>5, respectively.

Preferred human and murine nucleic acid sequences for NR6 or its derivatives include sequences from brain, liver, kidney, neonatal, embryonic, cancer or tumour-derived tissues.

Reference herein to a low stringency at 42° C. includes and encompasses from at least about 0% v/v to at least about 15% v/v formamide and from at least about 1 M to at least about 2 M salt for hybridization, and at least about 1 M to at least about 2 M salt for washing conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15M salt for hybridization, and at least about 0.01 M to at least about 0.15 M salt for washing conditions.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) (30). A detailed discussion of sequence analysis can be found in Unit 19.3 of Ausubel et al. (1998) 31).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25–30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (Marmur and Doty, 1962 (32). However, the $T_m$ of a duplex DNA decreases by 1° C. with every increase of 1% in the number of mismatch base pairs (Bonner and Laskey, 1974 (33)). Formamide is optional in these hybridization conditions. Accordingly, particularly preferred levels of stringency are defined as follows: low stringency is 6×SSC buffer, 0.1% w/v SDS at 25–42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The nucleic acid molecules contemplated by the present invention are generally in isolated form, and are preferably cDNA or genomic DNA molecules. In a particularly preferred embodiment, the nucleic acid molecules are in vectors and most preferably expression vectors to enable expression in a suitable host cell. Particularly useful host cells include prokaryotic cells, mammalian cells, yeast cells and insect cells. The cells may also be in the form of a cell line.

Accordingly, another aspect of the present invention provides an expression vector comprising a nucleic acid molecule encoding NR6 and CLC or modified forms thereof said expression vector capable of expression in a selected host cell.

Preferred percentage similarities to the reference nucleotide sequences include at least about 70%, more preferably at least about 80%, still more preferably at least about 90% and even more preferably at least about 95% or above.

Another aspect of the present invention provides a genetic construct comprising a sequence of nucleotides encoding NR6 or a derivative thereof having an amino acid sequence as set forth in <400>2 or having at least about 50% similarity to all or part thereof, said genetic construct further comprising a sequence of nucleotides encoding CLC or a modified form thereof.

Still yet another aspect of the present invention provides a genetic construct comprising a sequence of nucleotides encoding NR6 or a derivative thereof having an amino acid sequence as set forth in <400>4 or having at least about 50% similarity to all or part thereof, said genetic construct further comprising a sequence of nucleotides encoding CLC or a modified form thereof.

Even yet another aspect of the present invention provides a genetic construct comprising a sequence of nucleotides encoding NR6 or a derivative thereof having an amino acid sequence as set forth in <400>6 or having at least about 50% similarity to all or part thereof, said genetic construct further comprising a sequence of nucleotides encoding CLC or a modified form thereof.

A further aspect of the present invention provides a genetic construct comprising a sequence of nucleotides encoding NR6 or a derivative thereof having an amino acid sequence as set forth in <400>8 or having at least about 50% similarity to all or part thereof, said genetic construct further comprising a sequence of nucleotides encoding CLC or a modified form thereof.

Even yet a another aspect of the present invention provides a genetic construct comprising a sequence of nucleotides encoding NR6 or a derivative thereof having an amino acid sequence as set forth in <400>14 or having at least about 50% similarity to all or part thereof, said genetic construct further comprising a sequence of nucleotides encoding CLC or a modified form thereof.

Another aspect of the present invention provides a genetic construct comprising a sequence of nucleotides encoding NR6 or a derivative thereof having an amino acid sequence as set forth in one or more of <400>15 or having at least about 50% similarity to all or part thereof, said genetic construct further comprising a sequence of nucleotides encoding CLC or a modified form thereof.

Preferably, the percentage amino acid similarity is at least about 60%, more preferably at least about 70%, even more preferably at least about 80–85% and still even more preferably at least about 90–95% or greater.

The biologically active complex of the present invention may be in soluble form or may be expressed on a cell surface or conjugated or fused to a solid support or another molecule.

As stated above, the present invention further contemplates a range of derivatives of members of the complex. Derivatives include fragments, parts, portions, mutants, homologues and analogues of the polypeptides and corresponding genetic sequences. Derivatives also include single or multiple amino acid substitutions, deletions and/or additions to polypeptides or single or multiple nucleotide substitutions, deletions and/or additions to the genetic sequence encoding the polypeptides. "Additions" to amino acid sequences or nucleotide sequences include fusions with other peptides, polypeptides or proteins or fusions to nucleotide sequences. Reference herein to "NR6" or "CLC" or other polypeptides includes reference to all derivatives thereof including functional derivatives or immunologically interactive derivatives.

Analogues of the polypeptides contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

These types of modifications may be important to stabilize the complex if administered to an individual or for use as a diagnostic reagent.

Crosslinkers can be used, for example, to stabilize 3D conformations, using homobifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

TABLE 3

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrasine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |

TABLE 3-continued

| Non-conventional amino acid | Code |
|---|---|
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-Nmethylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

The present invention further contemplates chemical analogues of the polypeptides in the complex capable of acting as antagonists or agonists of the biologically active complex or of polypeptides interacting with or within the complex or which can act as functional analogues of the complex. Chemical analogues may not necessarily be derived from polypeptides in the complex but may share certain conformational similarities. Alternatively, chemical analogues may be specifically designed to mimic certain physiochemical properties of one or more polypeptides in the complex.

Chemical analogues may be chemically synthesized or may be detected following, for example, natural product screening.

Other derivatives contemplated by the present invention include a range of glycosylation variants from a completely unglycosylated molecule to a modified glycosylated molecule. Altered glycosylation patterns may result from expression of recombinant molecules in different host cells.

The identification of the complex permits the generation of a range of therapeutic molecules capable of modulating expression of polypeptides in the complex or modulating the activity of the complex. Modulators contemplated by the present invention includes agonists and antagonists of polypeptide expression. Antagonists of polypeptide expression include antisense molecules, ribozymes and co-suppression molecules. Agonists include molecules which increase promoter ability or interfere with negative regulatory mechanisms. Agonists of polypeptide include molecules which overcome any negative regulatory mechanism. Antagonists of the polypeptide include antibodies and inhibitor peptide fragments.

Another aspect of the present invention contemplates a method of modulating activity of the complex as hereinbefore described, said method comprising administering to a subject a modulating effective amount of a molecule for a time and under conditions sufficient to increase or decrease the biological activity of the complex. The molecule may be a proteinaceous molecule or a chemical entity and may also be a derivative of a polypeptide of the complex or its ligand or a chemical analogue or truncation mutant of a polypeptide of the complex or its ligand. The complex and its components such as but not limited to CLC, NR6 or a CLC-NR6 complex is proposed, in one embodiment, to possess neurotrophic activity.

The present invention, therefore, contemplates a pharmaceutical composition comprising the complex or a modulator of complex activity and one or more pharmaceutically acceptable carriers and/or diluents. These components are referred to as the "active ingredients".

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof, and vegetable oils. The proper fluidity can be maintained, for example, by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ug and 2000 mg of active compound. Alternative dosage amounts include from about 1 µg to about 1000 mg and from about 10 µg to about 500 mg.

The present invention also extends to forms suitable for topical application such as creams, lotions and gels as well as a range of "paints" which are applied to skin and through which the active ingredients are absorbed. In addition, the complex or components thereof may be associated with penetration or the TAT protein of HIV.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

Dosages may also be expressed per body weight of the recipient. For example, from about 10 ng to about 1000 mg/kg body weight, from about 100 ng to about 500 mg/kg body weight and for about 1 µg to above 250 mg/kg body weight may be administered.

The pharmaceutical composition may also comprise genetic molecules such as a vector capable of transfecting target cells where the vector carries a nucleic acid molecule capable of modulating levels of polypeptides involved the complex. The vector may, for example, be a viral vector.

Still another aspect of the present invention is directed to antibodies to the complex and its derivatives. Such antibodies may be monoclonal or polyclonal and may be selected from naturally occurring antibodies to the complex or may be specifically raised to the complex or derivatives thereof. In the case of the latter, the complex or its derivatives may first need to be associated with a carrier molecule. The antibodies and/or recombinant complex or its derivatives of the present invention are particularly useful as therapeutic or diagnostic agents. For example, complex antibodies or antibodies to its ligand may act as antagonists.

For example, the complex and its derivatives can be used to screen for naturally occurring antibodies to the complex. These may occur, for example in some autoimmune diseases. Alternatively, specific antibodies can be used to screen for the complex. Techniques for such assays are well known in the art and include, for example, sandwich assays and ELISA. Knowledge of complex levels may be important for diagnosis of certain disease conditions or a predisposition for a disease condition to occur or for monitoring certain therapeutic protocols.

Fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regimen.

For example, specific antibodies can be used to screen for the complex. The latter would be important, for example, as a means for screening for levels of the complex in a cell extract or other biological fluid or purifying the complex made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of the complex.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of NR6, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting the complex as hereinbefore described in a biological sample from a subject said method comprising contacting said biological sample with an antibody specific for the complex (or a component thereof) or its derivatives or homologues for a time and under conditions sufficient for an antibody complex to form, and then detecting said antibody.

The presence of the complex may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which might contain the complex including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the NR6 or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. from about room temperature to about 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

In another alternative method, a ligand or receptor of the complex is immobilized to a solid support and a biological sample containing the complex brought into contact with its immobilised ligand. Binding between the complex and its ligand or receptor can then be determined using an antibody to the complex or a component thereof which itself may be labelled with a reporter molecule or a further anti-immunoglobulin antibody labelled with a reporter molecule could be used to detect antibody bound to the complex.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention further contemplates a method for identifying agonists and antagonists of the biologically active complex as herein defined for use in therapy.

Accordingly, another aspect of the invention contemplates a method of identifying an agent capable of modulating the effects of a biologically active complex as herein defined, said method comprising screening for agents which are capable of interacting with the complex or interfering or otherwise antagonizing or promoting or otherwise agonizing interaction between the heterologous molecules of said complex.

The agent capable of agonizing or antagonizing interaction of the biologically active complex or between the heterologous molecules within the biologically active complex may be a proteinaceous or non-proteinaceous molecule. A proteinaceous molecule includes a peptide, polypeptide or protein or a complex thereof with, for example, a lipid, phospholipid or carbohydrate. A non-proteinaceous molecule includes a range of chemical entities including aromatic and/or pentanoid containing structures. Conveniently, the agent is identified following natural product screening of members of the biosphere such as but not limited to coral, plants and plant parts including bark, roots, flowers, leaves and stems, river beds, sea beds, micro-organisms, insects, soil and rock deposits as well as artic, antartic and even extraterrestrial (e.g. lunar) environments. The agent may also be identified following a screening of chemical libraries or using combinatorial chemical approaches.

Any number of screening procedures may be adopted to identify the agonists and antagonist. In one example, one or both heterologous molecules within the complex is/are linked to a reporter molecule such that upon interaction wither another molecule or a receptor or ligand, the reporter molecule provides an identifiable signal. An "identifiable signal" may be presence of a signal or absence of a signal. The amount or extent of signalling is then measured, quantitatively or qualitatively in the presence of potential agonists and/or antagonists. Any number of variations may be adopted to screen for agonists and antagonists. Variations of two hybrid screening and phage labelling may also be employed.

Once identified, the agonists and antagonists may be incorporated into a composition such as a pharmaceutical composition which comprises the agonist/antagonist and one or more pharmaceutically acceptable carriers and/or diluents. Alternatively, the agonist/antagonist may be provided genetically such as in the form of a DNA or RNA composition or the agonist/antagonist may comprise antisense, sense or riboyzme molecules.

A further aspect of the present invention contemplates the use of the biologically active complex or its functional derivatives in the manufacture of a medicament for the treatment of conditions resulting from aberrations in the complex or in reduced or excessive amounts of the complex.

Still a further aspect of the present invention contemplates a ligand or receptor for the complex such as in isolated or recombinant form, or a derivative of said ligand or receptor.

The present invention further contemplates knockout animals such as mice or other murine species for components of the complex gene including homozygous and heterozygous knockout animals. Such animals provide a particularly useful live in vivo model for studying the effects of the complex as well as screening for agents capable of acting as agonists or antagonists of the complex.

According to this embodiment there is provided a transgenic animal comprising a mutation in at least one allele of the gene encoding a component of the complex. Additionally, the present invention provides a transgenic animal comprising a mutation in two alleles of the gene encoding a component of the complex. Preferably, the transgenic animal is a murine animal such as a mouse or rat.

The present invention is further described by the following non-limiting Examples.

EXAMPLES

Standard methods for DNA cloning and protein expression are set forth in Sambrook et al. (Molecular Cloning: A Laboratory Manual, Cold Spring Harbor Laboratory Press, Cold Spring Harbor, N.Y. [1989]) and in Ausubel et al. Eds. (Current Protocols in Molecular Biology, Wiley, New York, N.Y. [1995]).

Example 1

Cloning of cDNA for CLC and Construction of the Expression Vectors

Plasmid vectors for the expression of untagged and $NH_2$-terminal haemagglutinin (HA) tagged CLC were prepared using PCR based approaches.

For untagged CLC a human CLC cDNA was cloned by PCR amplification from human foetal lung marathon-ready cDNA library (Clontech #7433-1). Based on the published sequence (GenBank AR002595 and AC005849), a sense primer with an EcoRI site at the 5' end: (5'-CGAATTC-CCCATGGACCTCCGAGCAG-3') (<400>21) and an antisense primer with a BamHI site at the 5' end: (5'-GGGATC-CTTTGAAGGGGGAGCGAAGAG-3') (<400>22) were synthesized and used in PCR to amplify the cDNA. After digestion with EcoRI and BamHI, the amplified fragment was ligated into the vector pCOS-1 (WO 98/11225). pCOS-1 is a mammalian expression vector with a G418-resistance marker.

Splice-overlap-extension PCR(SOE-PCR) was used to generate a CLC cDNA incorporating two modifications, a HA epitope tag (YPYDVPDYAS [<400>23]) and an IL-3 signal sequence (MVLASSTTSIHTMLLLLLMLF-HLGLQASIS [<400>24]) directly $NH_2$-terminal of the coding region of mature CLC ($Leu_{28}$). Fragment A was amplified using a sense primer (5'-CCATTTCAGGTGTCGTGAGG-3') (<400>25) and an anti-sense primer (5'-GTAGTCGGGCACGTCATAAGG ATACGAGATTGAAGCTTGGAG TCC-3') (<400>26) with the plasmid pEFBOS-S-FLAG (29) that contains the murine IL-3 signal sequence as a template. Fragment, B was amplified using a sense primer (5'-CCTTATGACGTGC-CCGACTACGCCAGTCTCAATCGCACAGGGGAC CCA-3' (<400>27) and an anti-sense primer with human CLC cDNA as a template. After mixing fragments A and B, the SOE-PCR product was amplified using the end primers. Following digestion with EcoRI and BamHI, the amplified fragment was ligated into the expression vectors pCOS-1 and pCHO-1 (WO 98/11225). pCHO-1 is a mammalian expression vector incorporating a dhfr (dihydrofolate reductase) gene, selectable in dhfr-deficient CHO cells.

Example 2

Co-Expression and Co-Immunoprecipitation of CLC with NR6

CHO cell lines expressing CLC alone, NR6 alone or co-expressing CLC and NR6 were established. Using a mammalian cell transfection kit (Stratagene Cat. No. 200285) dhfr-deficient CHO cells were transfected with:

(i) pCHO-1 encoding FLAG tagged NR6 (WO9811225) plus pCOS-1 encoding HA tagged CLC;

(ii) pCHO-1 encoding FLAG tagged NR6 alone;

(iii) pCHO-1 encoding HA tagged CLC alone.

The transfected cells were selected in medium (GIBCO Alpha-MEM medium without nucleic acids, with 10% v/v FCS) in the presence of 0.4 mg/ml G418.

For each immunoprecipitation, 1 ml of media conditioned by the indicated transfected cell line was used. Tagged proteins were precipitated using 0.05 ml of a suspension of either anti-FLAG M2-agarose (Sigma Cat. No. A1205) or anti-HA sepharose (BAbCo; Richmond, Calif., #AFC-101P). Immunoprecipitates were electrophoresed on SDS-PAGE, transferred to PVDF membrane and probed with an anti-HA antibody (Boehringer-Mannheim Cat. No. 1 666 851) or an anti-FLAG BioM2 antibody (Sigma Cat. No. F9291). Bound antibody was detected using an ECL detection system (Amersham-Pharmacia Biotech Cat. No. RPN2209). After stripping the bound antibodies, the membranes were re-probed with the same antibodies as used for the immunoprecipitation.

Figure 1A:
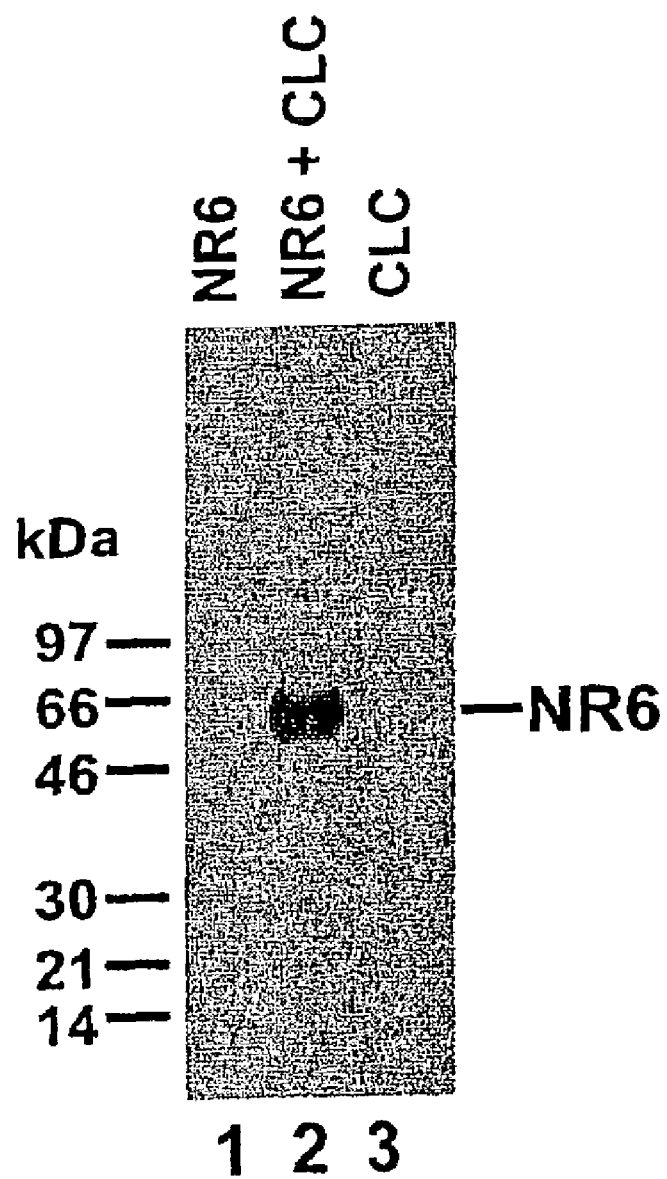
FIG. 1 is a photographic prepresentation of co-immunoprecipitation and Western blot analysis shows FLAG-NR6 forms a non-covalent heterodimer with HA-CLC.
Figure 1B:
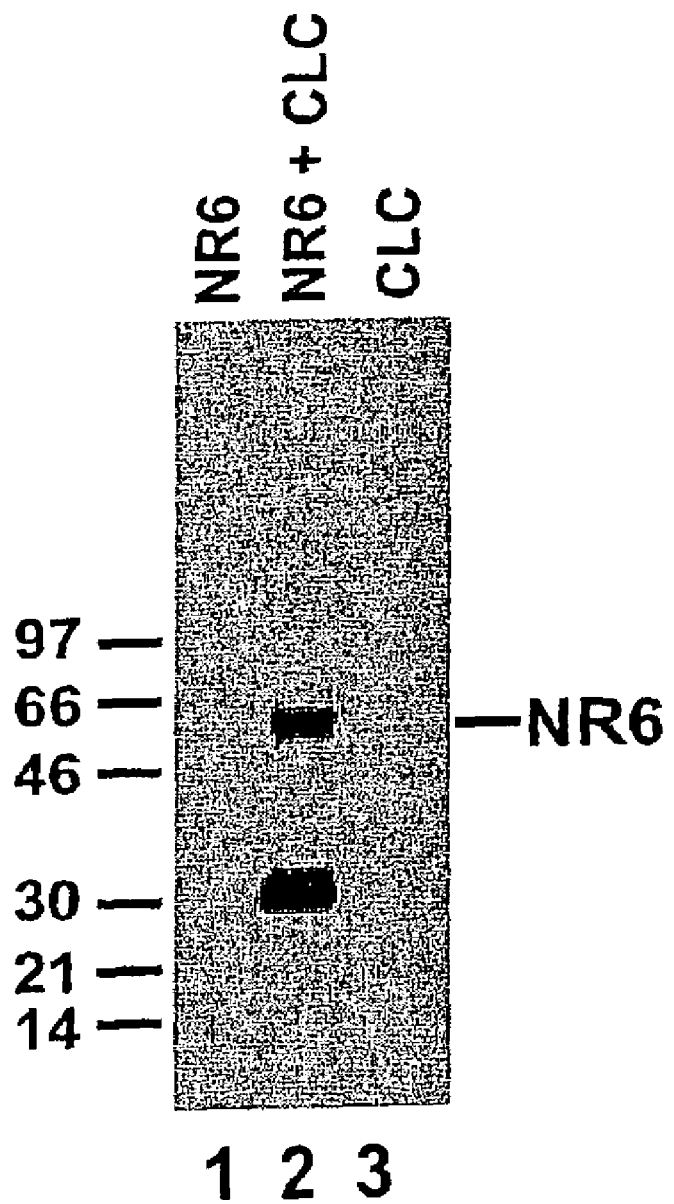
Figure 1C:
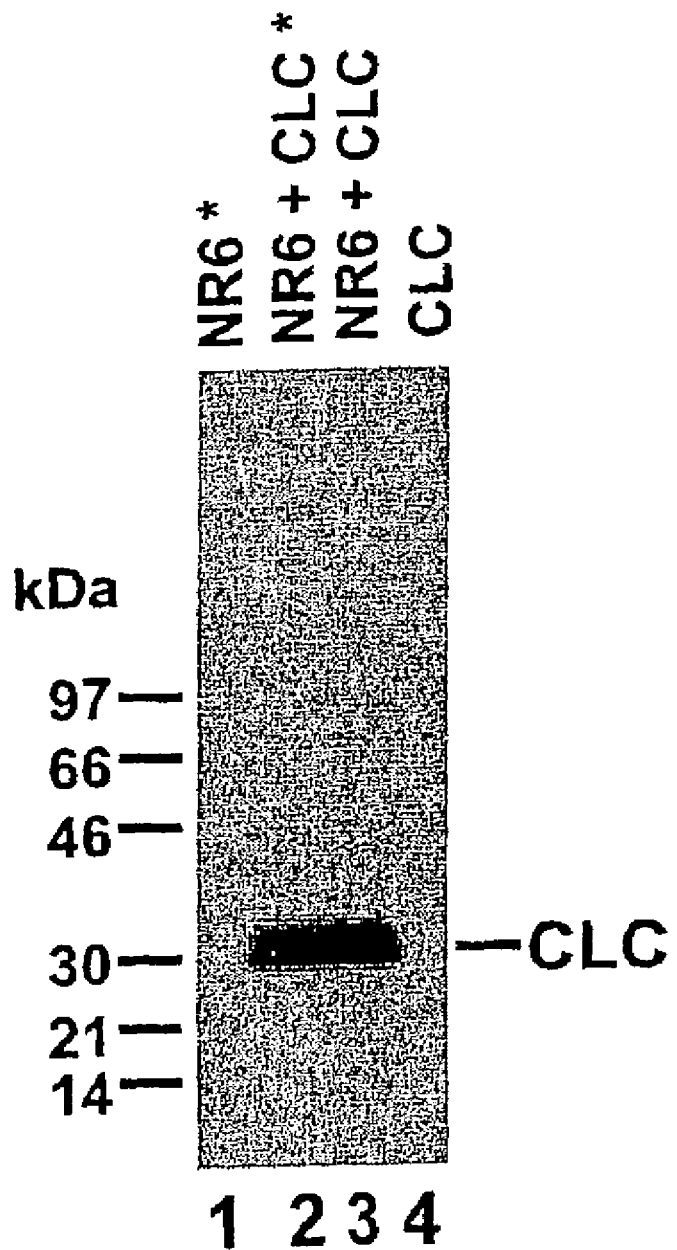
Figure 1D:
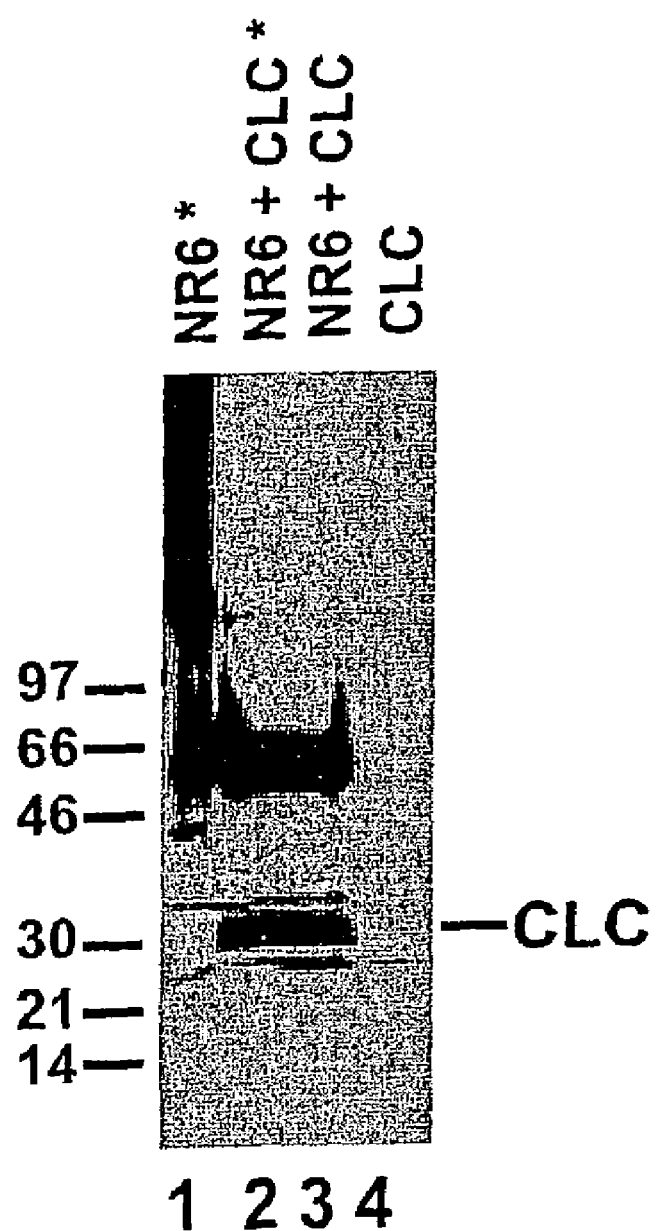

FLAG-tagged NR6 was co-immunoprecipitated with the HA-tagged CLC (FIG. 1A). In the same way, the HA-tagged CLC was co-immunoprecipitated with the FLAG-tagged NR6 (FIG. 1C). Following precipitation with anti-FLAG monomeric CLC was observed under both reducing and non-reducing conditions, suggesting that the NR6—CLC heterodimer is formed via a non-covalent interaction (FIG. 1C, lanes 2 and 3). When CLC was expressed alone it was not secreted into the conditioned medium (FIG. 1B, lane 3) but rather accumulated within cells. When NR6 was expressed alone, high-molecular weight aggregation of NR6 was observed under non-reducing conditions (FIG. 1D, lane 1). When CLC was co-expressed with NR6, CLC was efficiently secreted with NR6 (FIG. 1B, lane 2; note that the anti-FLAG mAb was incompletely stripped from the blot) and completely prevented the NR6 from forming aggregates (FIG. 1D, lanes 2 and 3).

Example 3

Preparation of Recombinant Heterodimeric CLC and NR6 Protein

Figures 2A, 2B:
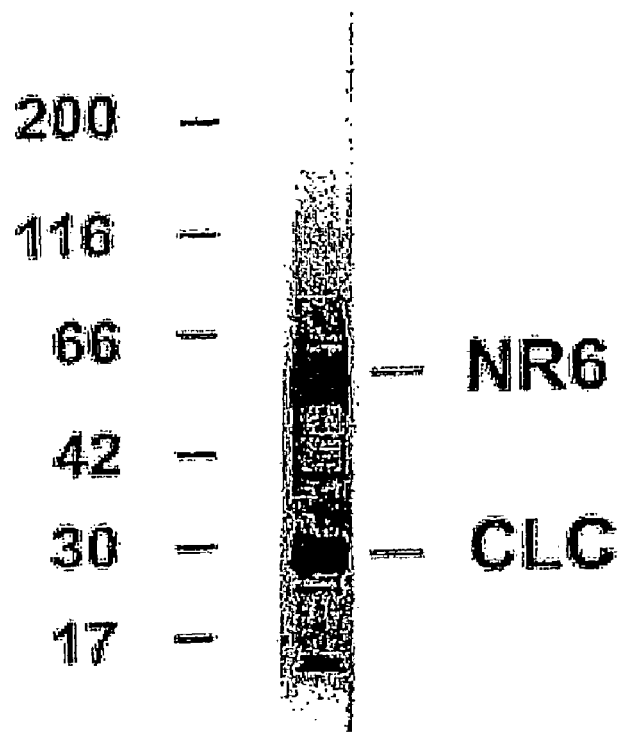

The pCHO-1 expression vector encoding FLAG-tagged NR6 and the pCOS-1 expression vector encoding CLC with the native signal sequence were transfected simultaneously into dhfr-deficient CHO cells using a mammalian cell transfection kit (Stratagene #200285). The introduced genes were amplified by addition of methotrexate (MTX) and by stepwise increase of the concentration of MTX and G418. The established cell line was cultured in GIBCO IMDM medium with 1% v/v FCS without MTX/G418 and the conditioned medium was collected on day 3. The recombinant secreted protein was purified by anti-FLAG M2-agarose (Sigma Cat. No. A1205) affinity chromatography according to the manufacturer's protocol. SDS-PAGE analysis identified a 27–29 kDa protein that co-purified with FLAG-tagged NR6 (55–60 kDa; FIG. 2A). The predicted molecular weight of unglycosylated CLC is 22 kDa. Electrophoresed proteins were transferred to PVDF and the 27–29 kDa band excised for sequencing. The $NH_2$-terminal amino acid sequence of the 27–29 kDa protein was determined to be LxRTGDPGPGPSI (<400>28), this is identical to the predicted N-terminal sequence of CLC (LNRTGDPGPGPSI [<400>29]). Asn (amino acid 2) of CLC forms a potential N-glycosylation site on CLC and is likely to be glycosylated.

Example 4

Figure 3A:
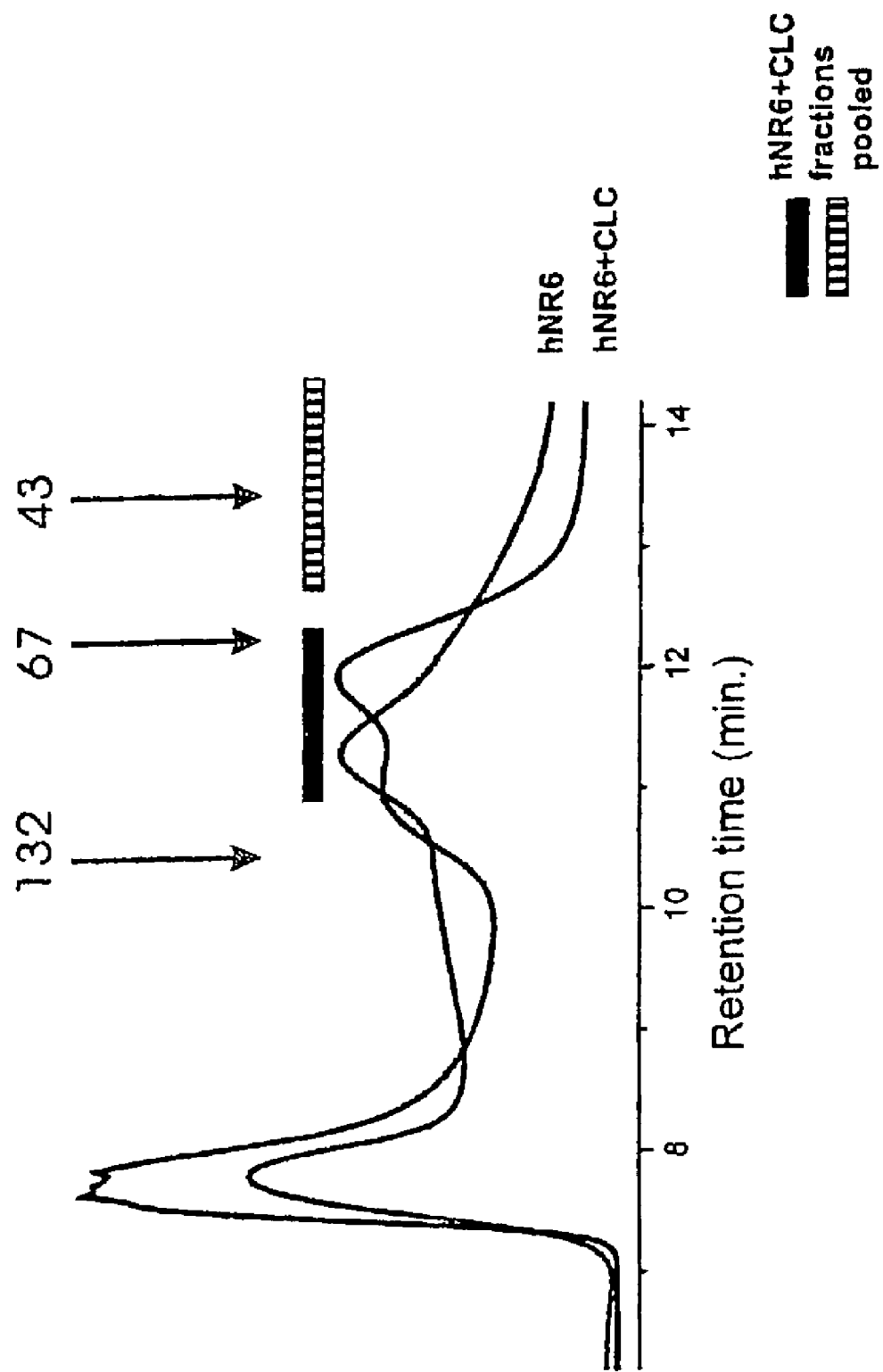
Figure 3B:
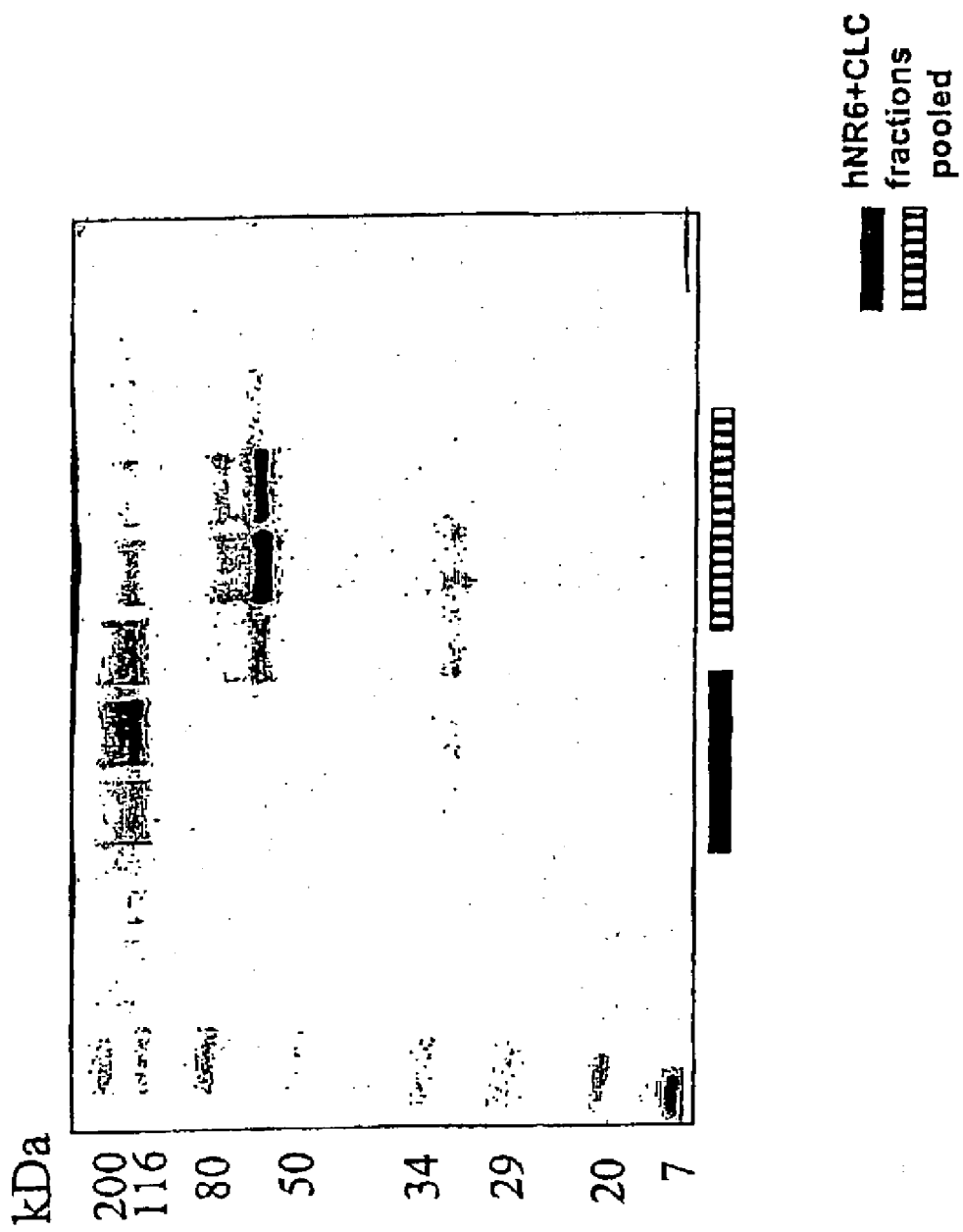

Structural Analysis of NR6—CLC Complexes and Demonstration of Biological Activity FLAG tagged NR6—CLC expressed in stable transfected CHO cells (see Example 3) was purified using anti-FLAG M2 affinity chromatography. The FLAG-NR6—CLC was displaced from the M2 column using 100 µg/ml FLAG peptide in 1% w/v ammonium bicarbonate. Material purified by M2 affinity was then subjected to size exclusion chromatography using a Pharmacia Superose 12 10/30 column at a flow rate of 1 ml/min on a Pharmacia Smart system. The elution profile (OD 215 nm) and non-reducing SDS-PAGE analysis of fractions collected at 0.5 minute intervals is shown in FIGS. 3A and 3B, respectively. In FIG. 3A, the elution profile of FLAG-NR-6-CLC is compared with that of purified FLAG-NR6 alone. Proteins species with an apparent molecular weight of approximately 120 kDa and 60 kDa were confirmed as dimeric and monomeric NR6, respectively. To confirm the identity of the lower molecular weight species running at approximately 29 kDa all fractions underlined were pooled and the pooled sample subjected to $NH_2$-terminal sequence analysis. Two distinct sequences were identified corresponding to FLAG-NR-6 and CLC (FIG. 4). The ratio at which the two sequences were detected (7:1, NR6:CLC) correlates well with staining intensity on the SDS-PAGE and like the SDS-PAGE also suggests that more NR6 is expressed than CLC. Together, the elution profile and SDS-PAGE analysis indicates that CLC is found in association (non-covalent) with both dimeric and monomeric NR6 species. The results further indicate that NR6 is secreted without associated CLC.

The inventors sought to determine whether CLC co-secreted with NR6 from mammalian cells displayed neurotrophic activity. Two pools of material (FIGS. 3A and B, underlined), one consisting of primarily dimeric NR6 and CLC (FIG. 3, underlined with solid bar) and the other containing primarily monomeric NR6 with CLC (FIG. 3, underlined with the hatched bar) were established using fractions eluted from the size exclusion column. By comparison with known protein standards these fractions were estimated to contain 70 µg/ml (approx. 10 µg/ml CLC) and 60 µg/ml (20 µg/ml CLC) of total protein, respectively. For assay, dorsal root ganglia were dissected from newborn C57/BL mice and dissociated to form a single cell suspension. Cells were plated in HLA plates which had been pre-treated with polyomithine and laminin, in Monomed media with 1% v/v FBS and cytokines as indicated. Forty-eight hrs later the number of surviving neurons was counted. Leukaemia inhibitory factor (LIF), a growth factor with known potent neurotrophic activity, was included as a positive control. Results are presented in FIG. 5 and clearly demonstrate neurotrophic activity in both FLAG-NR6—CLC samples tested. Although the pool containing primarily dimeric NR6 appears less active, this may in part be due to an overall lower proportion of CLC. Accordingly, CLC secreted with either dimeric or monomeric NR6 demonstrates neurotrophic activity Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Du, X. X. and Williams, D. A. (1994) *Blood* 83: 2023–2030.
2. Yang, Y. C. and Yin, T. (1992) *Biofactors* 4: 15–21.
3. Paul, S. R., Bennett, F., Calvetti, J. A., Kelleher, K., Wood, C. R., O'Hara, R. J. J., Leary, A. C., Sibley, B., Clark, S. C., Williams, D. A. and Yang, Y.-C. (1990) *Proc. Natl. Acad. Sci. USA* 87: 7512.
4. Musashi, M., Clark, S. C., Sudo, T., Urdal, D. L., and Ogawa, M. (1991) *Blood* 78: 1448–1451.
5. Schibler, K. R., Yang, Y. C. and Christensen, R. D. (1992) *Blood* 80: 900–3.
6. Tsuji, K., Lyman, S. D., Sudo, T., Clark, S. C., and Ogawa, M. (1992) *Blood* 79: 2855–60.
7. Burstein, S. A., Mei, R. L., Henthorn, J., Friese, P. and turner, K. (1992) *J. Cell. Physiol.* 153: 305–12.
8. Hangoc, G., Yin, T., Cooper, S., Schendel, P., Yang, Y. C. and Broxmeyer, H. E. (1993) *Blood* 81: 965–72.
9. Teramura, M., Kobayashi, S., Hoshino, S., Oshimi, K. and Mizoguchi, H. (1992) *Blood* 79: 327–31.
10. Yonemura, Y., Kawakita, M., Masuda, T., Fujimoto, K., Kato, K. and Takatsuki, K. (1992) *Exp. Hematol.* 20: 1011–6.
11. Baumann, H. and Schendel, P. (1991) *J. Biol. Chem.* 266: 20424–7.
12. Kawashima, I., Ohsumi, J., Mita-Honjo, K., Shimoda-Takano, K., Ishikawa, H., Sakakibara, S., Miyadai, K. and Takiguchi, Y. (1991) *Febs. Lett.* 283: 199–202.
13. Keller, D.C., Du, X. X., Srour, E. f., Hoffman, R. and Williams, D. A. (1993) *Blood* 82: 1428–35.
14. Sambrook et al (1989) Cloning: A Laboratory Manual. Cold Spring Harbour Laboratory, Cold Spring Harbour, NY.
15. Chirgwin et al (1979) *Biochemistry* 18: 5294–5299.

16. Mizushima and Nagata (1990) *Nucl. Acids Res.*, 18: 5322.
17. *FEBS Lett* (1994) 356: 244–248.
18. Bazan, J. F. (1990) *Proc Natl Acad Sci USA*, 87, 6934–8
19. de Vos, A. M., Ultsch, M. and Kossiakoff, A. A. (1992) *Science*, 255, 306–12
20. Layton, M. J., Cross, B. A., Metcalf, D., Ward, L. D., Simpson, R. J. and Nicola, N. A. (1992) *Proceedings of the National Academy of Sciences of the United States of America* 89: 8616–8620
21. Taga, T., Hibi, M., Hirata, T., Tamasaki, K., Tasukawa, K., Matsuda, T., Hirano, T. and Kishimoto, T. (1989) *Cell* 58: 573–581
22. Merberg, D. M., Wolf, S. F. and Clark, S. C. (1992) Sequence similarity between NKSF and the IL-6/G-CSF family (1992) *Immunology Today* 13: 77–78
23. Cearing, D. P. and Cosman, D. (1991) *Cell* 66:9–10
24. Wrighton, N. C., Farrell, F. X., Chang, R., Kashyap, A. K., Barbone, F. P., Mulcahy, L. S., Johnson, D. L., Barrett, R. W., Jolliffe, L. K. and Dower, W. J. (1996) *Science* 273:458–464.
25. Cwirla, S. E., Balasubramanian, P., Duffin, D. J., Wagstrom, C. R., Gates, C. M., Singer, S. C., Davis, A. M., Tansik, R. L., Mattheakis, L. C., Boytos, C. M., Schatz, P. J., Baccanari, D. P., Wrighton, N. C., Barret, R. W. and Dower, W. J. (1997) *Science* 276: 1696–9, 1997
26. *BBRC* 262: 132–138, 1999.
27. Sambrook et al (1989) Molecular Cloning: A Laboratory Manual. Cold Spring Harbor Laboratories, Cold Spring Harbor, N.Y.
28. Ausubel et al, *Current Protocols in Molecular Biology*, 1995.
29. Hilton et al, *Proc. Natl. Acad. Sci. USA* 93(1): 497–501, 1996.
30. Altschul et al., *Nucl. Acids Res.* 25:3389, 1997.
31. Ausubel et al., "Current Protocols in Molecular Biology", John Wiley & Sons Inc, 1994–1998, Chapter 15.
32. Marmur and Doty *J. Mol. Biol.* 5: 109, 1962.
33. Bonner and Laskey *Eur. J. Biochem.* 46: 83, 1974.

The invention claimed is:

1. An isolated biologically active complex comprising at least one NR6 polypeptide and at least one cardiotrophin-like cytokine (CLC) polypeptide, wherein said CLC polypeptide comprises an amino acid sequence having at least 95% identity with SEQ ID NO: 20, said NR6 polypeptide comprises an amino acid sequence having at least 95% identity with SEQ ID NO: 14, and wherein said complex has neurotrophic activity.

2. An isolated biologically active complex comprising at least one NR6 polypeptide and at least one cardiotrophin-like cytokine (CLC) polypeptide or a, wherein said CLC polypeptide comprises an amino acid sequence encoded by a nucleotide sequence which has at least 95% identity with SEQ ID NO: 19 or hybridizes to the complement of SEQ ID NO: 19 under high stringency conditions, said NR6 polypeptide comprises an amino acid sequence encoded by a nucleotide sequence which has at least 95% identity with SEQ ID NO: 13, or hybridizes to the complement of SEQ ID NO: 13 under said high stringency conditions, wherein said high stringency conditions comprise hybridization in at least about 31% v/v to at least about 50% formamide and at least about 0.01 M to at least about 0.15 M salt, and washing in 0.1×SSC and 0.1% SDS at a temperature of at least 65° C., and wherein said complex has neurotrophic activity.

3. A composition comprising an isolated biologically active complex according to claim 1 or 2 and at least one pharmaceutically active carrier or diluent.

4. A genetic construct comprising a first nucleotide sequence encoding a NR6 polypeptide and a second nucleotide sequence encoding a CLC polypeptide, wherein said CLC polypeptide comprises an amino acid sequence having at least 95% identity with SEQ ID NO: 20, and wherein said NR6 polypeptide comprises an amino acid sequence having at least 95% identity with SEQ ID NO: 14.

5. A genetic construct comprising a first nucleotide sequence encoding a NR6 polypeptide and a second nucleotide sequence encoding a CLC polypeptide, wherein said CLC polypeptide comprises an amino acid sequence encoded by a nucleotide sequence which has at least 95% identity with SEQ ID NO: 19 or hybridizes to the complement of SEQ ID NO: 19 under high stringency conditions, said NR6 polypeptide comprises an amino acid sequence encoded by a nucleotide sequence which has at least 95% identity with SEQ ID NO: 13, or hybridizes to the complement of SEQ ID NO: 13 under said high stringency conditions, wherein said high stringency conditions comprise hybridization in at least about 31% v/v to at least about 50% formamide and at least about 0.01 M to at least about 0.15 M salt, and washing in 0.1×SSC and 0.1% SDS at a temperature of at least 65° C., and wherein said complex has neurotrophic activity.

6. An expression vector comprising a genetic construct according to claim 4 or 5.

* * * * *

SEQUENCE LISTING

```
<160> NUMBER OF SEQ ID NOS: 31

<210> SEQ ID NO 1
<211> LENGTH: 1629
<212> TYPE: DNA
<213> ORGANISM: Murine
<220> FEATURE:
<221> NAME/KEY: CDS
<222> LOCATION: (124)..(1365)
<220> FEATURE:
<221> NAME/KEY: 5'UTR
<222> LOCATION: (1)..(123)
<220> FEATURE:
<221> NAME/KEY: 3'UTR
<222> LOCATION: (1366)..(1629)

<400> SEQUENCE: 1
ggcacgagct tcgctgtccg cgcccagtga cgcgcgtgcg gacccgagcc ccaatctgca      60
ccccgcagac tcgcccccgc cccataccgg cgttgcagtc accgcccgtt gcgcgccacc     120 ccc atg ccc gcg ggt cgc ccg ggc ccc gtc gcc caa tcc gcg cgg cgg      168
    Met Pro Ala Gly Arg Pro Gly Pro Val Ala Gln Ser Ala Arg Arg
    1               5                   10                  15 ccg ccg cgg ccg ctg tcc tcg ctg tgg tcg cct ctg ttg ctc tgt gtc      216
Pro Pro Arg Pro Leu Ser Ser Leu Trp Ser Pro Leu Leu Leu Cys Val
                20                  25                  30 ctc ggg gtg cct cgg ggc gga tcg gga gcc cac aca gct gta atc agc      264
Leu Gly Val Pro Arg Gly Gly Ser Gly Ala His Thr Ala Val Ile Ser
            35                  40                  45 ccc cag gac ccc acc ctt ctc atc ggc tcc tcc ctg caa gct acc tgc      312
Pro Gln Asp Pro Thr Leu Leu Ile Gly Ser Ser Leu Gln Ala Thr Cys
        50                  55                  60 tct ata cat gga gac aca cct ggg gcc acc gct gag ggg ctc tac tgg      360
Ser Ile His Gly Asp Thr Pro Gly Ala Thr Ala Glu Gly Leu Tyr Trp
65                  70                  75 acc ctc aat ggt cgc cgc ctg ccc tct gag ctg tcc cgc ctc ctt aac      408
Thr Leu Asn Gly Arg Arg Leu Pro Ser Glu Leu Ser Arg Leu Leu Asn
    80                  85                  90                  95 acc tcc acc ctg gcc ctg gcc ctg gct aac ctt aat ggg tcc agg cag      456
Thr Ser Thr Leu Ala Leu Ala Leu Ala Asn Leu Asn Gly Ser Arg Gln
                100                 105                 110
```

-continued

```
cag tca gga gac aat ctg gtg tgt cac gcc cga gac ggc agc att ctg       504
Gln Ser Gly Asp Asn Leu Val Cys His Ala Arg Asp Gly Ser Ile Leu
            115                 120                 125 gct ggc tcc tgc ctc tat gtt ggc ttg ccc cct gag aag ccc ttt aac       552
Ala Gly Ser Cys Leu Tyr Val Gly Leu Pro Pro Glu Lys Pro Phe Asn
            130                 135                 140 atc agc tgc tgg tcc cgg aac atg aag gat ctc acg tgc cgc tgg aca       600
Ile Ser Cys Trp Ser Arg Asn Met Lys Asp Leu Thr Cys Arg Trp Thr
145                 150                 155 ccg ggt gca cac ggg gag aca ttc tta cat acc aac tac tcc ctc aag       648
Pro Gly Ala His Gly Glu Thr Phe Leu His Thr Asn Tyr Ser Leu Lys
160                 165                 170                 175 tac aag ctg agg tgg tac ggt cag gat aac aca tgt gag gag tac cac       696
Tyr Lys Leu Arg Trp Tyr Gly Gln Asp Asn Thr Cys Glu Glu Tyr His
                180                 185                 190 act gtg ggc cct cac tca tgc cat atc ccc aag gac ctg gcc ctc ttc       744
Thr Val Gly Pro His Ser Cys His Ile Pro Lys Asp Leu Ala Leu Phe
            195                 200                 205 act ccc tat gag atc tgg gtg gaa gcc acc aat cgc cta ggc tca gca       792
Thr Pro Tyr Glu Ile Trp Val Glu Ala Thr Asn Arg Leu Gly Ser Ala
            210                 215                 220 aga tct gat gtc ctc aca ctg gat gtc ctg gac gtg gtg acc acg gac       840
Arg Ser Asp Val Leu Thr Leu Asp Val Leu Asp Val Val Thr Thr Asp
225                 230                 235 ccc cca ccc gac gtg cac gtg agc cgc gtt ggg ggc ctg gag gac cag       888
Pro Pro Pro Asp Val His Val Ser Arg Val Gly Gly Leu Glu Asp Gln
240                 245                 250                 255 ctg agt gtg cgc tgg gtc tca cca cca gct ctc aag gat ttc ctc ttc       936
Leu Ser Val Arg Trp Val Ser Pro Pro Ala Leu Lys Asp Phe Leu Phe
                260                 265                 270 caa gcc aag tac cag atc cgc tac cgc gtg gag gac agc gtg gac tgg       984
Gln Ala Lys Tyr Gln Ile Arg Tyr Arg Val Glu Asp Ser Val Asp Trp
            275                 280                 285 aag gtg gtg gat gac gtc agc aac cag acc tcc tgc cgt ctc gcg ggc      1032
Lys Val Val Asp Asp Val Ser Asn Gln Thr Ser Cys Arg Leu Ala Gly
            290                 295                 300 ctg aag ccc ggc acc gtt tac ttc gtc caa gtg cgt tgt aac cca ttc      1080
Leu Lys Pro Gly Thr Val Tyr Phe Val Gln Val Arg Cys Asn Pro Phe
305                 310                 315 ggg atc tat ggg tcg aaa aag gcg gga atc tgg agc gag tgg agc cac      1128
Gly Ile Tyr Gly Ser Lys Lys Ala Gly Ile Trp Ser Glu Trp Ser His
320                 325                 330                 335 ccc acc gct gcc tcc acc cct cga agt gag cgc ccg ggc ccg ggc ggc      1176
Pro Thr Ala Ala Ser Thr Pro Arg Ser Glu Arg Pro Gly Pro Gly Gly
                340                 345                 350 ggg gtg tgc gag ccg cgg ggc ggc gag ccc agc tcg ggc ccg gtg cgg      1224
Gly Val Cys Glu Pro Arg Gly Gly Glu Pro Ser Ser Gly Pro Val Arg
            355                 360                 365 cgc gag ctc aag cag ttc ctc ggc tgg ctc aag aag cac gca tac tgc      1272
Arg Glu Leu Lys Gln Phe Leu Gly Trp Leu Lys Lys His Ala Tyr Cys
            370                 375                 380 tcg aac ctt agt ttc cgc ctg tac gac cag tgg cgt gct tgg atg cag      1320
Ser Asn Leu Ser Phe Arg Leu Tyr Asp Gln Trp Arg Ala Trp Met Gln
385                 390                 395 aag tca cac aag acc cga aac cag gtc ctg ccg gct aaa ctc taa          1365
Lys Ser His Lys Thr Arg Asn Gln Val Leu Pro Ala Lys Leu
400                 405                 410 ggataggcca tcctcctgct gggtcagacc tggaggctca cctgaattgg agcccctctg   1425
```

-continued

```
taccatctgg gcaacaaaga aacctaccag aggctggggc acaatgagct cccacaacca    1485
cagctttggt ccacatgatg gtcacacttg gatatacccc agtgtgggta aggttggggt    1545
attgcagggc ctcccaacaa tctctttaaa taaataaagg agttgttcag gtaaaaaaaa    1605
aaaaaaaaaa aaaaaaaaaa aaaa                                          1629
```

<210> SEQ ID NO 2
<211> LENGTH: 413
<212> TYPE: PRT
<213> ORGANISM: Murine

<400> SEQUENCE: 2

```
Met Pro Ala Gly Arg Pro Gly Pro Val Ala Gln Ser Ala Arg Arg Pro
  1               5                  10                  15

Pro Arg Pro Leu Ser Ser Leu Trp Ser Pro Leu Leu Leu Cys Val Leu
             20                  25                  30

Gly Val Pro Arg Gly Gly Ser Gly Ala His Thr Ala Val Ile Ser Pro
         35                  40                  45

Gln Asp Pro Thr Leu Leu Ile Gly Ser Ser Leu Gln Ala Thr Cys Ser
     50                  55                  60

Ile His Gly Asp Thr Pro Gly Ala Thr Ala Glu Gly Leu Tyr Trp Thr
 65                  70                  75                  80

Leu Asn Gly Arg Arg Leu Pro Ser Glu Leu Ser Arg Leu Leu Asn Thr
                 85                  90                  95

Ser Thr Leu Ala Leu Ala Leu Ala Asn Leu Asn Gly Ser Arg Gln Gln
            100                 105                 110

Ser Gly Asp Asn Leu Val Cys His Ala Arg Asp Gly Ser Ile Leu Ala
        115                 120                 125

Gly Ser Cys Leu Tyr Val Gly Leu Pro Pro Glu Lys Pro Phe Asn Ile
    130                 135                 140

Ser Cys Trp Ser Arg Asn Met Lys Asp Leu Thr Cys Arg Trp Thr Pro
145                 150                 155                 160

Gly Ala His Gly Glu Thr Phe Leu His Thr Asn Tyr Ser Leu Lys Tyr
                165                 170                 175

Lys Leu Arg Trp Tyr Gly Gln Asp Asn Thr Cys Glu Glu Tyr His Thr
            180                 185                 190

Val Gly Pro His Ser Cys His Ile Pro Lys Asp Leu Ala Leu Phe Thr
        195                 200                 205

Pro Tyr Glu Ile Trp Val Glu Ala Thr Asn Arg Leu Gly Ser Ala Arg
    210                 215                 220

Ser Asp Val Leu Thr Leu Asp Val Leu Asp Val Val Thr Thr Asp Pro
225                 230                 235                 240

Pro Pro Asp Val His Val Ser Arg Val Gly Gly Leu Glu Asp Gln Leu
                245                 250                 255

Ser Val Arg Trp Val Ser Pro Pro Ala Leu Lys Asp Phe Leu Phe Gln
            260                 265                 270

Ala Lys Tyr Gln Ile Arg Tyr Arg Val Glu Asp Ser Val Asp Trp Lys
        275                 280                 285

Val Val Asp Asp Val Ser Asn Gln Thr Ser Cys Arg Leu Ala Gly Leu
    290                 295                 300

Lys Pro Gly Thr Val Tyr Phe Val Gln Val Arg Cys Asn Pro Phe Gly
305                 310                 315                 320

Ile Tyr Gly Ser Lys Lys Ala Gly Ile Trp Ser Glu Trp Ser His Pro
                325                 330                 335
```

-continued

```
        Thr Ala Ala Ser Thr Pro Arg Ser Glu Arg Pro Gly Pro Gly Gly Gly
                    340                 345                 350

Val Cys Glu Pro Arg Gly Gly Glu Pro Ser Ser Gly Pro Val Arg Arg
                    355                 360                 365

Glu Leu Lys Gln Phe Leu Gly Trp Leu Lys Lys His Ala Tyr Cys Ser
                    370                 375                 380

Asn Leu Ser Phe Arg Leu Tyr Asp Gln Trp Arg Ala Trp Met Gln Lys
        385                 390                 395                 400

Ser His Lys Thr Arg Asn Gln Val Leu Pro Ala Lys Leu
                    405                 410

<210> SEQ ID NO 3
<211> LENGTH: 1673
<212> TYPE: DNA
<213> ORGANISM: Murine
<220> FEATURE:
<221> NAME/KEY: CDS
<222> LOCATION: (125)..(1402)
<220> FEATURE:
<221> NAME/KEY: 5'UTR
<222> LOCATION: (1)..(124)
<220> FEATURE:
<221> NAME/KEY: 3'UTR
<222> LOCATION: (1403)..(1673)

<400> SEQUENCE: 3
ggcacgagct cgctgtccg cgcccagtga cgcgcgtgcg gacccgagcc ccaatctgca      60
ccccgcagac tcgcccccgc ccataccgg cgttgcagtc accgcccgtt gcgcgccacc     120 ccca atg ccc gcg ggt cgc ccg ggc ccc gtc gcc caa tcc gcg cgg cgg    169
     Met Pro Ala Gly Arg Pro Gly Pro Val Ala Gln Ser Ala Arg Arg
     1               5                  10                  15 ccg ccg cgg ccg ctg tcc tcg ctg tgg tcg cct ctg ttg ctc tgt gtc    217
Pro Pro Arg Pro Leu Ser Ser Leu Trp Ser Pro Leu Leu Leu Cys Val
                20                  25                  30 ctc ggg gtg cct cgg ggc gga tcg gga gcc cac aca gct gta atc agc    265
Leu Gly Val Pro Arg Gly Gly Ser Gly Ala His Thr Ala Val Ile Ser
            35                  40                  45 ccc cag gac ccc acc ctt ctc atc ggc tcc tcc ctg caa gct acc tgc    313
Pro Gln Asp Pro Thr Leu Leu Ile Gly Ser Ser Leu Gln Ala Thr Cys
        50                  55                  60 tct ata cat gga gac aca cct ggg gcc acc gct gag ggg ctc tac tgg    361
Ser Ile His Gly Asp Thr Pro Gly Ala Thr Ala Glu Gly Leu Tyr Trp
    65                  70                  75 acc ctc aat ggt cgc cgc ctg ccc tct gag ctg tcc cgc ctc ctt aac    409
Thr Leu Asn Gly Arg Arg Leu Pro Ser Glu Leu Ser Arg Leu Leu Asn
 80                  85                  90                  95 acc tcc acc ctg gcc ctg gcc ctg gct aac ctt aat ggg tca agg cag    457
Thr Ser Thr Leu Ala Leu Ala Leu Ala Asn Leu Asn Gly Ser Arg Gln
                100                 105                 110 cag tca gga gac aat ctg gtg tgt cac gcc cga gac ggc agc att ctg    505
Gln Ser Gly Asp Asn Leu Val Cys His Ala Arg Asp Gly Ser Ile Leu
            115                 120                 125 gct ggc tcc tgc ctc tat gtt ggc ttg ccc cct gag aag ccc ttt aac    553
Ala Gly Ser Cys Leu Tyr Val Gly Leu Pro Pro Glu Lys Pro Phe Asn
        130                 135                 140 atc agc tgc tgg tcc cgg aac atg aag gat ctc acg tgc cgc tgg aca    601
Ile Ser Cys Trp Ser Arg Asn Met Lys Asp Leu Thr Cys Arg Trp Thr
    145                 150                 155 ccg ggt gca cac ggg gag aca ttc tta cat acc aac tac tcc ctc aag    649
Pro Gly Ala His Gly Glu Thr Phe Leu His Thr Asn Tyr Ser Leu Lys
160                 165                 170                 175
```

-continued

| | | |
|---|---|---|
| tac aag ctg agg tgg tac ggt cag gat aac aca tgt gag gag tac cac<br>Tyr Lys Leu Arg Trp Tyr Gly Gln Asp Asn Thr Cys Glu Glu Tyr His<br>                   180                        185                   190 | 697 |
| act gtg ggc cct cac tca tgc cat atc ccc aag gac ctg gcc ctc ttc<br>Thr Val Gly Pro His Ser Cys His Ile Pro Lys Asp Leu Ala Leu Phe<br>       195                     200                   205 | 745 |
| act ccc tat gag atc tgg gtg gaa gcc acc aat cgc cta ggc tca gca<br>Thr Pro Tyr Glu Ile Trp Val Glu Ala Thr Asn Arg Leu Gly Ser Ala<br>           210                    215                   220 | 793 |
| aga tct gat gtc ctc aca ctg gat gtc ctg gac gtg gtg acc acg gac<br>Arg Ser Asp Val Leu Thr Leu Asp Val Leu Asp Val Val Thr Thr Asp<br>225                   230                    235 | 841 |
| ccc cca ccc gac gtg cac gtg agc cgc gtt ggg ggc ctg gag gac cag<br>Pro Pro Pro Asp Val His Val Ser Arg Val Gly Gly Leu Glu Asp Gln<br>240                   245                250                 255 | 889 |
| ctg agt gtg cgc tgg gtc tca cca cca gct ctc aag gat ttc ctc ttc<br>Leu Ser Val Arg Trp Val Ser Pro Pro Ala Leu Lys Asp Phe Leu Phe<br>           260                   265                270 | 937 |
| caa gcc aag tac cag atc cgc tac cgc gtg gag gac agc gtg gac tgg<br>Gln Ala Lys Tyr Gln Ile Arg Tyr Arg Val Glu Asp Ser Val Asp Trp<br>               275                   280                285 | 985 |
| aag gtg gtg gat gac gtc agc aac cag acc tcc tgc cgt ctc gcg ggc<br>Lys Val Val Asp Asp Val Ser Asn Gln Thr Ser Cys Arg Leu Ala Gly<br>      290                     295                   300 | 1033 |
| ctg aag ccc ggc acc gtt tac ttc gtc caa gtg cgt tgt aac cca ttc<br>Leu Lys Pro Gly Thr Val Tyr Phe Val Gln Val Arg Cys Asn Pro Phe<br>305                   310                    315 | 1081 |
| ggg atc tat ggg tcg aaa aag gcg gga atc tgg agc gag tgg agc cac<br>Gly Ile Tyr Gly Ser Lys Lys Ala Gly Ile Trp Ser Glu Trp Ser His<br>320                   325                  330                335 | 1129 |
| ccc acc gct gcc tcc acc cct cga agt gag cgc ccg ggc ccg ggc ggc<br>Pro Thr Ala Ala Ser Thr Pro Arg Ser Glu Arg Pro Gly Pro Gly Gly<br>                    340                   345                350 | 1177 |
| ggg gtg tgc gag ccg cgg ggc ggc gag ccc agc tcg ggc ccg gtg cgg<br>Gly Val Cys Glu Pro Arg Gly Gly Glu Pro Ser Ser Gly Pro Val Arg<br>               355                   360                365 | 1225 |
| cgc gag ctc aag cag ttc ctc ggc tgg ctc aag aag cac gca tac tgc<br>Arg Glu Leu Lys Gln Phe Leu Gly Trp Leu Lys Lys His Ala Tyr Cys<br>      370                     375                   380 | 1273 |
| tcg aac ctt agt ttc cgc ctg tac gac cag tgg cgt gct tgg atg cag<br>Ser Asn Leu Ser Phe Arg Leu Tyr Asp Gln Trp Arg Ala Trp Met Gln<br>385                   390                    395 | 1321 |
| aag tca cac aag acc cga aac cag gac gag ggg atc ctg cct tcg ggc<br>Lys Ser His Lys Thr Arg Asn Gln Asp Glu Gly Ile Leu Pro Ser Gly<br>400                   405                  410                415 | 1369 |
| aga cgg ggt gcg gcg aga ggt cct gcc ggt taa actctaagga taggccatcc<br>Arg Arg Gly Ala Ala Arg Gly Pro Ala Gly<br>                   420                   425 | 1422 |
| tcctgctggg tcagacctgg aggctcacct gaattggagc ccctctgtac catctgggca | 1482 |
| acaaagaaac ctaccagagg ctggggcaca atgagctccc acaaccacag ctttggtcca | 1542 |
| catgatggtc acacttggat ataccccagt gtgggtaagg ttggggtatt gcagggcctc | 1602 |
| ccaacaatct cttttaaataa ataaaggagt tgttcaggta aaaaaaaaaa aaaaaaaaaa | 1662 |
| aaaaaaaaaa a | 1673 |

<210> SEQ ID NO 4
<211> LENGTH: 425
<212> TYPE: PRT

<213> ORGANISM: Murine

<400> SEQUENCE: 4

```
Met Pro Ala Gly Arg Gly Pro Val Ala Gln Ser Ala Arg Arg Pro
 1               5                  10                  15

Pro Arg Pro Leu Ser Ser Leu Trp Ser Pro Leu Leu Cys Val Leu
                 20                  25                  30

Gly Val Pro Arg Gly Gly Ser Gly Ala His Thr Ala Val Ile Ser Pro
             35                  40                  45

Gln Asp Pro Thr Leu Leu Ile Gly Ser Ser Leu Gln Ala Thr Cys Ser
 50                  55                  60

Ile His Gly Asp Thr Pro Gly Ala Thr Ala Glu Gly Leu Tyr Trp Thr
 65                  70                  75                  80

Leu Asn Gly Arg Arg Leu Pro Ser Glu Leu Ser Arg Leu Leu Asn Thr
                 85                  90                  95

Ser Thr Leu Ala Leu Ala Leu Ala Asn Leu Asn Gly Ser Arg Gln Gln
                100                 105                 110

Ser Gly Asp Asn Leu Val Cys His Ala Arg Asp Gly Ser Ile Leu Ala
                115                 120                 125

Gly Ser Cys Leu Tyr Val Gly Leu Pro Pro Glu Lys Pro Phe Asn Ile
130                 135                 140

Ser Cys Trp Ser Arg Asn Met Lys Asp Leu Thr Cys Arg Trp Thr Pro
145                 150                 155                 160

Gly Ala His Gly Glu Thr Phe Leu His Thr Asn Tyr Ser Leu Lys Tyr
                165                 170                 175

Lys Leu Arg Trp Tyr Gly Gln Asp Asn Thr Cys Glu Glu Tyr His Thr
                180                 185                 190

Val Gly Pro His Ser Cys His Ile Pro Lys Asp Leu Ala Leu Phe Thr
                195                 200                 205

Pro Tyr Glu Ile Trp Val Glu Ala Thr Asn Arg Leu Gly Ser Ala Arg
210                 215                 220

Ser Asp Val Leu Thr Leu Asp Val Leu Asp Val Val Thr Thr Asp Pro
225                 230                 235                 240

Pro Pro Asp Val His Val Ser Arg Val Gly Gly Leu Glu Asp Gln Leu
                245                 250                 255

Ser Val Arg Trp Val Ser Pro Pro Ala Leu Lys Asp Phe Leu Phe Gln
                260                 265                 270

Ala Lys Tyr Gln Ile Arg Tyr Arg Val Glu Asp Ser Val Asp Trp Lys
                275                 280                 285

Val Val Asp Asp Val Ser Asn Gln Thr Ser Cys Arg Leu Ala Gly Leu
290                 295                 300

Lys Pro Gly Thr Val Tyr Phe Val Gln Val Arg Cys Asn Pro Phe Gly
305                 310                 315                 320

Ile Tyr Gly Ser Lys Lys Ala Gly Ile Trp Ser Glu Trp Ser His Pro
                325                 330                 335

Thr Ala Ala Ser Thr Pro Arg Ser Glu Arg Pro Gly Pro Gly Gly Gly
                340                 345                 350

Val Cys Glu Pro Arg Gly Gly Glu Pro Ser Ser Gly Pro Val Arg Arg
                355                 360                 365

Glu Leu Lys Gln Phe Leu Gly Trp Leu Lys Lys His Ala Tyr Cys Ser
                370                 375                 380

Asn Leu Ser Phe Arg Leu Tyr Asp Gln Trp Arg Ala Trp Met Gln Lys
385                 390                 395                 400
```

```
Ser His Lys Thr Arg Asn Gln Asp Glu Gly Ile Leu Pro Ser Gly Arg
            405                 410                 415
Arg Gly Ala Ala Arg Gly Pro Ala Gly
            420                 425

<210> SEQ ID NO 5
<211> LENGTH: 938
<212> TYPE: DNA
<213> ORGANISM: Murine
<220> FEATURE:
<221> NAME/KEY: CDS
<222> LOCATION: (1)..(468)

<400> SEQUENCE: 5 ggc acc gtt tac ttc gtc caa gtg cgt tgt aac cca ttc ggg atc tat      48
Gly Thr Val Tyr Phe Val Gln Val Arg Cys Asn Pro Phe Gly Ile Tyr
  1               5                  10                  15 ggg tcg aaa aag gcg gga atc tgg agc gag tgg agc cac ccc acc gct      96
Gly Ser Lys Lys Ala Gly Ile Trp Ser Glu Trp Ser His Pro Thr Ala
             20                  25                  30 gcc tcc acc cct cga agt gag cgc ccg ggc ccg ggc ggc ggg gtg tgc     144
Ala Ser Thr Pro Arg Ser Glu Arg Pro Gly Pro Gly Gly Gly Val Cys
         35                  40                  45 gag ccg cgg ggc ggc gag ccc agc tcg ggc ccg gtg cgg cgc gag ctc     192
Glu Pro Arg Gly Gly Glu Pro Ser Ser Gly Pro Val Arg Arg Glu Leu
     50                  55                  60 aag cag ttc ctc ggc tgg ctc aag aag cac gca tac tgc tcg aac ctt     240
Lys Gln Phe Leu Gly Trp Leu Lys Lys His Ala Tyr Cys Ser Asn Leu
 65                  70                  75                  80 agt ttc cgc ctg tac gac cag tgg cgt gct tgg atg cag aag tca cac     288
Ser Phe Arg Leu Tyr Asp Gln Trp Arg Ala Trp Met Gln Lys Ser His
                 85                  90                  95 aag acc cga aac cag gta gga aag ttg ggg gag gct tgc gtg ggg ggt     336
Lys Thr Arg Asn Gln Val Gly Lys Leu Gly Glu Ala Cys Val Gly Gly
            100                 105                 110 aaa gga gca gag gaa gag aga gac ccg ggt gag cag cct cca caa cac     384
Lys Gly Ala Glu Glu Glu Arg Asp Pro Gly Glu Gln Pro Pro Gln His
        115                 120                 125 cgc act ctt ctt tcc aag cac agg acg agg gga tcc tgc cct cgg gca     432
Arg Thr Leu Leu Ser Lys His Arg Thr Arg Gly Ser Cys Pro Arg Ala
    130                 135                 140 gac ggg gtg cgg cga gag gta agg ggg tct ggg tga gtggggccta          478
Asp Gly Val Arg Arg Glu Val Arg Gly Ser Gly
145                 150                 155 cagcagtcta gatgaggccc tttcccctcc ttcggtgttg ctcaaaggga tctcttagtg   538
ctcatttcac ccactgcaaa gagcccagg ttttactgca tcatcaagtt gctgaagggt    598
ccaggcttaa tgtggcctct tttctgccct caggtcctgc cggctaaact ctaaggatag   658
gccatcctcc tgctgggtca gacctggagg ctcacctgaa ttggagcccc tctgtaccta   718
tctgggcaac aaagaaacct accatgaggc tgggcacaa tgagctccca caaccacagc    778
tttggtccac atgatggtca cacttggata taccccagtg tgggtaaggt tggggtattg   838
cagggcctcc caacaatctc tttaaataaa taaaggagtt gttcaggtaa aaaaaaaaa    898 aaaaaaaaa aaaaaaaaa aaaaaaaaa aaaaaaaaa                             938

<210> SEQ ID NO 6
<211> LENGTH: 155
<212> TYPE: PRT
<213> ORGANISM: Murine
```

-continued

```
<400> SEQUENCE: 6

Gly Thr Val Tyr Phe Val Gln Val Arg Cys Asn Pro Phe Gly Ile Tyr
 1               5                  10                  15

Gly Ser Lys Lys Ala Gly Ile Trp Ser Glu Trp Ser His Pro Thr Ala
            20                  25                  30

Ala Ser Thr Pro Arg Ser Glu Arg Pro Gly Pro Gly Gly Gly Val Cys
        35                  40                  45

Glu Pro Arg Gly Gly Glu Pro Ser Ser Gly Pro Val Arg Arg Glu Leu
    50                  55                  60

Lys Gln Phe Leu Gly Trp Leu Lys Lys His Ala Tyr Cys Ser Asn Leu
65                  70                  75                  80

Ser Phe Arg Leu Tyr Asp Gln Trp Arg Ala Trp Met Gln Lys Ser His
                85                  90                  95

Lys Thr Arg Asn Gln Val Gly Lys Leu Gly Glu Ala Cys Val Gly Gly
            100                 105                 110

Lys Gly Ala Glu Glu Arg Asp Pro Gly Glu Gln Pro Pro Gln His
        115                 120                 125

Arg Thr Leu Leu Ser Lys His Arg Thr Arg Gly Ser Cys Pro Arg Ala
    130                 135                 140

Asp Gly Val Arg Arg Glu Val Arg Gly Ser Gly
145                 150                 155

<210> SEQ ID NO 7
<211> LENGTH: 834
<212> TYPE: DNA
<213> ORGANISM: Murine
<220> FEATURE:
<221> NAME/KEY: CDS
<222> LOCATION: (1)..(834)

<400> SEQUENCE: 7 ccc acc ctt ctc atc ggc tcc tcc ctg caa gct acc tgc tct ata cat     48
Pro Thr Leu Leu Ile Gly Ser Ser Leu Gln Ala Thr Cys Ser Ile His
 1               5                  10                  15 gga gac aca cct ggg gcc acc gct gag ggg ctc tac tgg acc ctc aat     96
Gly Asp Thr Pro Gly Ala Thr Ala Glu Gly Leu Tyr Trp Thr Leu Asn
            20                  25                  30 ggt cgc cgc ctg ccc tct gag ctg tcc cgc ctc ctt aac acc tcc acc    144
Gly Arg Arg Leu Pro Ser Glu Leu Ser Arg Leu Leu Asn Thr Ser Thr
        35                  40                  45 ctg gcc ctg gcc ctg gct aac ctt aat ggg tcc agg cag cag tca gga    192
Leu Ala Leu Ala Leu Ala Asn Leu Asn Gly Ser Arg Gln Gln Ser Gly
    50                  55                  60 gac aat ctg gtg tgt cac gcc cga gac ggc agc att ctg gct ggc tcc    240
Asp Asn Leu Val Cys His Ala Arg Asp Gly Ser Ile Leu Ala Gly Ser
65                  70                  75                  80 tgc ctc tat gtt ggc ttg ccc cct gag aag ccc ttt aac atc agc tgc    288
Cys Leu Tyr Val Gly Leu Pro Pro Glu Lys Pro Phe Asn Ile Ser Cys
                85                  90                  95 tgg tcc cgg aac atg aag gat ctc acg tgc cgc tgg aca ccg ggt gca    336
Trp Ser Arg Asn Met Lys Asp Leu Thr Cys Arg Trp Thr Pro Gly Ala
            100                 105                 110 cac ggg gag aca ttc tta cat acc aac tac tcc ctc aag tac aag ctg    384
His Gly Glu Thr Phe Leu His Thr Asn Tyr Ser Leu Lys Tyr Lys Leu
        115                 120                 125 agg tgg tac ggt cag gat aac aca tgt gag gag tac cac act gtg ggg    432
Arg Trp Tyr Gly Gln Asp Asn Thr Cys Glu Glu Tyr His Thr Val Gly
    130                 135                 140
```

```
ccc cac tca tgc cat atc ccc aag gac ctg gcc ctc ttc act ccc tat      480
Pro His Ser Cys His Ile Pro Lys Asp Leu Ala Leu Phe Thr Pro Tyr
145                 150                 155                 160 gag atc tgg gtg gaa gcc acc aat cgc cta ggc tca gca aga tct gat      528
Glu Ile Trp Val Glu Ala Thr Asn Arg Leu Gly Ser Ala Arg Ser Asp
                165                 170                 175 gtc ctc aca ctg gat gtc ctg gac gtg gtg acc acg gac ccc cca ccc      576
Val Leu Thr Leu Asp Val Leu Asp Val Val Thr Thr Asp Pro Pro Pro
            180                 185                 190 gac gtg cac gtg agc cgc gtt ggg ggc ctg gag gac cag ctg agt gtg      624
Asp Val His Val Ser Arg Val Gly Gly Leu Glu Asp Gln Leu Ser Val
        195                 200                 205 cgc tgg gtc tca cca cca gct ctc aag gat ttc ctc ttc caa gcc aag      672
Arg Trp Val Ser Pro Pro Ala Leu Lys Asp Phe Leu Phe Gln Ala Lys
    210                 215                 220 tac cag atc cgc tac cgc gtg gag gac agc gtg gac tgg aag gtg gtg      720
Tyr Gln Ile Arg Tyr Arg Val Glu Asp Ser Val Asp Trp Lys Val Val
225                 230                 235                 240 gat gac gtc agc aac cag acc tcc tgc cgt ctc gcg ggc ctg aag ccc      768
Asp Asp Val Ser Asn Gln Thr Ser Cys Arg Leu Ala Gly Leu Lys Pro
                245                 250                 255 ggc acc gtt tac ttc gtc caa gtg cgt tgt aac cca ttc ggg atc tat      816
Gly Thr Val Tyr Phe Val Gln Val Arg Cys Asn Pro Phe Gly Ile Tyr
            260                 265                 270 ggg tcg aaa aag gcg gga                                              834
Gly Ser Lys Lys Ala Gly
        275
```

<210> SEQ ID NO 8
<211> LENGTH: 278
<212> TYPE: PRT
<213> ORGANISM: Murine

<400> SEQUENCE: 8

```
Pro Thr Leu Leu Ile Gly Ser Ser Leu Gln Ala Thr Cys Ser Ile His
1               5                   10                  15

Gly Asp Thr Pro Gly Ala Thr Ala Glu Gly Leu Tyr Trp Thr Leu Asn
            20                  25                  30

Gly Arg Arg Leu Pro Ser Glu Leu Ser Arg Leu Leu Asn Thr Ser Thr
        35                  40                  45

Leu Ala Leu Ala Leu Ala Asn Leu Asn Gly Ser Arg Gln Gln Ser Gly
    50                  55                  60

Asp Asn Leu Val Cys His Ala Arg Asp Gly Ser Ile Leu Ala Gly Ser
65                  70                  75                  80

Cys Leu Tyr Val Gly Leu Pro Pro Glu Lys Pro Phe Asn Ile Ser Cys
                85                  90                  95

Trp Ser Arg Asn Met Lys Asp Leu Thr Cys Arg Trp Thr Pro Gly Ala
            100                 105                 110

His Gly Glu Thr Phe Leu His Thr Asn Tyr Ser Leu Lys Tyr Lys Leu
        115                 120                 125

Arg Trp Tyr Gly Gln Asp Asn Thr Cys Glu Glu Tyr His Thr Val Gly
    130                 135                 140

Pro His Ser Cys His Ile Pro Lys Asp Leu Ala Leu Phe Thr Pro Tyr
145                 150                 155                 160

Glu Ile Trp Val Glu Ala Thr Asn Arg Leu Gly Ser Ala Arg Ser Asp
                165                 170                 175

Val Leu Thr Leu Asp Val Leu Asp Val Val Thr Thr Asp Pro Pro Pro
            180                 185                 190
```

```
Asp Val His Val Ser Arg Val Gly Gly Leu Glu Asp Gln Leu Ser Val
        195                 200                 205
Arg Trp Val Ser Pro Pro Ala Leu Lys Asp Phe Leu Phe Gln Ala Lys
    210                 215                 220
Tyr Gln Ile Arg Tyr Arg Val Glu Asp Ser Val Asp Trp Lys Val Val
225                 230                 235                 240
Asp Asp Val Ser Asn Gln Thr Ser Cys Arg Leu Ala Gly Leu Lys Pro
                245                 250                 255
Gly Thr Val Tyr Phe Val Gln Val Arg Cys Asn Pro Phe Gly Ile Tyr
            260                 265                 270
Gly Ser Lys Lys Ala Gly
            275

<210> SEQ ID NO 9
<211> LENGTH: 1391
<212> TYPE: DNA
<213> ORGANISM: Murine
<220> FEATURE:
<221> NAME/KEY: CDS
<222> LOCATION: (1)..(1053)

<400> SEQUENCE: 9
```

| | | | | | | | | | | | | | | | | |
|---|---|---|---|---|---|---|---|---|---|---|---|---|---|---|---|---|
| acc | ctc | aac | ggg | cgc | cgc | ctg | ccc | cct | gag | ctc | tcc | cgt | gta | ctc | aac | 48 |
| Thr | Leu | Asn | Gly | Arg | Arg | Leu | Pro | Pro | Glu | Leu | Ser | Arg | Val | Leu | Asn | |
| 1 | | | | 5 | | | | | 10 | | | | | 15 | | |
| gcc | tcc | acc | ttg | gct | ctg | gcc | ctg | gcc | aac | ctc | aat | ggg | tcc | agg | cag | 96 |
| Ala | Ser | Thr | Leu | Ala | Leu | Ala | Leu | Ala | Asn | Leu | Asn | Gly | Ser | Arg | Gln | |
| | | | 20 | | | | | 25 | | | | | 30 | | | |
| cgg | tcg | ggg | gac | aac | ctc | gtg | tgc | cac | gcc | cgt | gac | ggc | agc | atc | ctg | 144 |
| Arg | Ser | Gly | Asp | Asn | Leu | Val | Cys | His | Ala | Arg | Asp | Gly | Ser | Ile | Leu | |
| | | 35 | | | | | 40 | | | | | 45 | | | | |
| gct | ggc | tcc | tgc | ctc | tat | gtt | ggc | ctg | ccc | cca | gag | aaa | ccc | gtc | aac | 192 |
| Ala | Gly | Ser | Cys | Leu | Tyr | Val | Gly | Leu | Pro | Pro | Glu | Lys | Pro | Val | Asn | |
| | 50 | | | | | 55 | | | | | 60 | | | | | |
| atc | agc | tgc | tgg | tcc | aag | aac | atg | aag | gac | ttg | acc | tgc | cgc | tgg | acg | 240 |
| Ile | Ser | Cys | Trp | Ser | Lys | Asn | Met | Lys | Asp | Leu | Thr | Cys | Arg | Trp | Thr | |
| 65 | | | | | 70 | | | | | 75 | | | | | 80 | |
| cca | ggg | gcc | cac | ggg | gag | acc | ttc | ctc | cac | acc | aac | tac | tcc | ctc | aag | 288 |
| Pro | Gly | Ala | His | Gly | Glu | Thr | Phe | Leu | His | Thr | Asn | Tyr | Ser | Leu | Lys | |
| | | | | 85 | | | | | 90 | | | | | 95 | | |
| tac | aag | ctt | agg | tgg | tat | ggc | cag | gac | aac | aca | tgt | gag | gag | tac | cac | 336 |
| Tyr | Lys | Leu | Arg | Trp | Tyr | Gly | Gln | Asp | Asn | Thr | Cys | Glu | Glu | Tyr | His | |
| | | | 100 | | | | | 105 | | | | | 110 | | | |
| aca | gtg | ggg | ccc | cac | tcc | tgc | cac | atc | ccc | aag | gac | ctg | gct | ctc | ttt | 384 |
| Thr | Val | Gly | Pro | His | Ser | Cys | His | Ile | Pro | Lys | Asp | Leu | Ala | Leu | Phe | |
| | | 115 | | | | | 120 | | | | | 125 | | | | |
| acg | ccc | tat | gag | atc | tgg | gtg | gag | gcc | acc | aac | cgc | ctg | ggc | tct | gcc | 432 |
| Thr | Pro | Tyr | Glu | Ile | Trp | Val | Glu | Ala | Thr | Asn | Arg | Leu | Gly | Ser | Ala | |
| | 130 | | | | | 135 | | | | | 140 | | | | | |
| cgc | tcc | gat | gta | ctc | acg | ctg | gat | atc | ctg | gat | gtg | gtg | acc | acg | gac | 480 |
| Arg | Ser | Asp | Val | Leu | Thr | Leu | Asp | Ile | Leu | Asp | Val | Val | Thr | Thr | Asp | |
| 145 | | | | | 150 | | | | | 155 | | | | | 160 | |
| ccc | ccg | ccc | gac | gtg | cac | gtg | agc | cgc | gtc | ggg | ggc | ctg | gag | gac | cag | 528 |
| Pro | Pro | Pro | Asp | Val | His | Val | Ser | Arg | Val | Gly | Gly | Leu | Glu | Asp | Gln | |
| | | | | 165 | | | | | 170 | | | | | 175 | | |
| ctg | agc | gtg | cgc | tgg | gtg | tcg | cca | ccc | gcc | ctc | aag | gat | ttc | ctc | ttt | 576 |
| Leu | Ser | Val | Arg | Trp | Val | Ser | Pro | Pro | Ala | Leu | Lys | Asp | Phe | Leu | Phe | |
| | | | 180 | | | | | 185 | | | | | 190 | | | |
| caa | gcc | aaa | tac | cag | atc | cgc | tac | cga | gtg | gag | gac | agt | gtg | gac | tgg | 624 |

```
                Gln Ala Lys Tyr Gln Ile Arg Tyr Arg Val Glu Asp Ser Val Asp Trp
                        195                 200                 205 aag gtg gtg gac gat gtg agc aac cag acc tcc tgc cgc ctg gcc ggc              672
Lys Val Val Asp Asp Val Ser Asn Gln Thr Ser Cys Arg Leu Ala Gly
            210                 215                 220 ctg aaa ccc ggc acc gtg tac ttc gtg caa gtg cgc tgc aac ccc ttt              720
Leu Lys Pro Gly Thr Val Tyr Phe Val Gln Val Arg Cys Asn Pro Phe
225                 230                 235                 240 ggc atc tat ggc tcc aag aaa gcc ggg atc tgg agt gag tgg agc cac              768
Gly Ile Tyr Gly Ser Lys Lys Ala Gly Ile Trp Ser Glu Trp Ser His
                245                 250                 255 ccc aca gcc gcc tcc act ccc cgc agt gag cgc ccg ggc ccg ggc ggc              816
Pro Thr Ala Ala Ser Thr Pro Arg Ser Glu Arg Pro Gly Pro Gly Gly
            260                 265                 270 ggg gcg tgc gaa ccg cgg ggc gga gag ccg agc tcg ggg ccg gtg cgg              864
Gly Ala Cys Glu Pro Arg Gly Gly Glu Pro Ser Ser Gly Pro Val Arg
275                 280                 285 cgc gag ctc aag cag ttc ctg ggc tgg ctc aag aag cac gcg tac tgc              912
Arg Glu Leu Lys Gln Phe Leu Gly Trp Leu Lys Lys His Ala Tyr Cys
        290                 295                 300 tcc aac ctc agc ttc cgc ctc tac gac cag tgg cga gcc tgg atg cag              960
Ser Asn Leu Ser Phe Arg Leu Tyr Asp Gln Trp Arg Ala Trp Met Gln
305                 310                 315                 320 aag tcg cac aag acc cgc aac cag cac agg acg agg gga tcc tgc cct             1008
Lys Ser His Lys Thr Arg Asn Gln His Arg Thr Arg Gly Ser Cys Pro
                325                 330                 335 cgg gca gac ggg gca cgg cga gag gtc ctg cca gat aag ctg tag                 1053
Arg Ala Asp Gly Ala Arg Arg Glu Val Leu Pro Asp Lys Leu
            340                 345                 350 gggctcaggc cacctccct gccacgtgga gacgcagagg ccgaacccaa actggggcca            1113
cctctgtacc ctcacttcag ggcacctgag cccctcagca ggagctgggg tggcccctga            1173
gctccaacgg ccataacagc tctgactccc acgtgaggcc acctttgggt gcaccccagt            1233
gggtgtgtgt gtgtgtgtga gggttggttg agttgcctag aaccctgcc agggctgggg             1293 gtgagaaggg gagtcattac tccccattac ctagggcccc tccaaaagag tccttttaaa            1353
taaatgagct atttaggtgc aaaaaaaaaa aaaaaaaa                                    1391

<210> SEQ ID NO 10
<211> LENGTH: 350
<212> TYPE: PRT
<213> ORGANISM: Murine

<400> SEQUENCE: 10

Thr Leu Asn Gly Arg Arg Leu Pro Pro Glu Leu Ser Arg Val Leu Asn
1               5                   10                  15

Ala Ser Thr Leu Ala Leu Ala Leu Ala Asn Leu Asn Gly Ser Arg Gln
            20                  25                  30

Arg Ser Gly Asp Asn Leu Val Cys His Ala Arg Asp Gly Ser Ile Leu
        35                  40                  45

Ala Gly Ser Cys Leu Tyr Val Gly Leu Pro Pro Glu Lys Pro Val Asn
    50                  55                  60

Ile Ser Cys Trp Ser Lys Asn Met Lys Asp Leu Thr Cys Arg Trp Thr
65                  70                  75                  80

Pro Gly Ala His Gly Glu Thr Phe Leu His Thr Asn Tyr Ser Leu Lys
                85                  90                  95

Tyr Lys Leu Arg Trp Tyr Gly Gln Asp Asn Thr Cys Glu Glu Tyr His
            100                 105                 110
```

```
Thr Val Gly Pro His Ser Cys His Ile Pro Lys Asp Leu Ala Leu Phe
            115                 120                 125

Thr Pro Tyr Glu Ile Trp Val Glu Ala Thr Asn Arg Leu Gly Ser Ala
        130                 135                 140

Arg Ser Asp Val Leu Thr Leu Asp Ile Leu Asp Val Val Thr Thr Asp
145                 150                 155                 160

Pro Pro Pro Asp Val His Val Ser Arg Val Gly Gly Leu Glu Asp Gln
                165                 170                 175

Leu Ser Val Arg Trp Val Ser Pro Ala Leu Lys Asp Phe Leu Phe
            180                 185                 190

Gln Ala Lys Tyr Gln Ile Arg Tyr Arg Val Glu Asp Ser Val Asp Trp
        195                 200                 205

Lys Val Val Asp Asp Val Ser Asn Gln Thr Ser Cys Arg Leu Ala Gly
        210                 215                 220

Leu Lys Pro Gly Thr Val Tyr Phe Val Gln Val Arg Cys Asn Pro Phe
225                 230                 235                 240

Gly Ile Tyr Gly Ser Lys Lys Ala Gly Ile Trp Ser Glu Trp Ser His
                245                 250                 255

Pro Thr Ala Ala Ser Thr Pro Arg Ser Glu Arg Pro Gly Pro Gly Gly
            260                 265                 270

Gly Ala Cys Glu Pro Arg Gly Gly Glu Pro Ser Ser Gly Pro Val Arg
        275                 280                 285

Arg Glu Leu Lys Gln Phe Leu Gly Trp Leu Lys Lys His Ala Tyr Cys
        290                 295                 300

Ser Asn Leu Ser Phe Arg Leu Tyr Asp Gln Trp Arg Ala Trp Met Gln
305                 310                 315                 320

Lys Ser His Lys Thr Arg Asn Gln His Arg Thr Arg Gly Ser Cys Pro
                325                 330                 335

Arg Ala Asp Gly Ala Arg Arg Glu Val Leu Pro Asp Lys Leu
            340                 345                 350

<210> SEQ ID NO 11
<211> LENGTH: 6663
<212> TYPE: DNA
<213> ORGANISM: Murine

<400> SEQUENCE: 11
cccagaactc ttggacgctg aggcaggagg attcccaagt ttcaagacag tgtgtttcta      60
ggtaatgaga ccctgtcaag aaaagaaaag aaataaagag acaagaaaat gtttataggc     120
tgtgagacag cttggtgggt aagggcact tgcctccaat caagatgacc tcagccccat      180
ccctaggaat ccatggtaga aggagaaagc aaactcgcag ctgctgacct ccatacatgt     240
gctccaatgt gcacacacac agggagacat aatcaattaa taggatgtat ttgcttagat     300
ttgagtaggc atttatgact gatgttttaa aattttttatt tgattttatg aaatatacc    360
tgtttgtatt tggtttggtt tggtttgagt tttgtttatt tgagacaggg cttctctgtg     420
tagtcctggc tgtccttgga actcactctg tagaccaggc tggccttgaa ctcagaaatc     480
cgcctgcttg tgcttcccaa gtgcttagat taaggtgtg cactgccatt cagcaaaatt      540
gcatacttta accccagtat ttgggaggca gaggcagact aatgtgtgaa ttccaggcta     600
gccaaggata cagagtgaga ccctattctt accctccccc cccaaaaccc caaaatgtat     660
tttgtgcttg tgtatgtaca tgtgtgttgc agcacgtaaa tgtccaagga caacttgtag     720
aagttctctc cgttcacagt ctaagtcctg aattcaaact aaggtcctca ggcttagcca     780
```

```
cagtcttctt tatgtactga gccatttcac tggccctgga ttgactgatg aattaattt    840
tgagataagg tctcttgtag ctctagctag gctcaaacta tgaactccca aggtcatctt   900
gagctgctgg tactcttgct tccaccccaa gtggtggaat gatactcagg cagcacttct   960
ctggggaagg ggctggcctt ggccttgatt ttgttgcctc agcttcaatg agtgcttggg  1020
tctcgttgtt tctttctttt atctgtgaaa tgggtgaaca cctgttcaag acttcctgac  1080
tcttgaaaca tccaggcagg gtgagggact tgaagtgggc tcatcccatg cctaacaaag  1140
tgtcgtcttt gacccagac acagctgtaa tcagccccca ggaccccacc cttctcatcg    1200
gctcctccct gcaagctacc tgctctatac atggagacac acctggggcc accgctgagg  1260
ggctctactg gaccttcaat ggtcgccgcc tgccctctga gctgtcccgc ctccttaaca  1320
cctccaccct ggccctggcc ctggctaacc ttaatgggtc caggcagcag tcaggagaca  1380
atctggtgtg tcacgcccga gacggcagca ttctggctgg ctcctgcctc tatgttggct  1440
gtaagtgggg ccccagacac tcagagatag atggggttg gcaatgacag atttagagcc   1500
tgggtcttct gtcctggggc agagccatgg gctctcactt gcatgcaggc atggtcatac  1560
ccagcacagg cattgcaact ctagggacag ctgtggctgc actgtcccct gtgtacccca  1620
cagctttaga aaagctgtca tgttttcctt gtagtgcccc ctgagaagcc ctttaacatc  1680
agctgctggt cccggaacat gaaggatctc acgtgccgct ggacaccggg tgcacacggg  1740
gagacattct tacataccaa ctactccctc aagtacaagc tgaggttggt acccagccaa  1800
gccttgctgt gtgacttctg caatactta ccttctctga tcaaatatgt tcctgttat    1860
gaactcaaaa gggactctcg cacctccaca ggtggtacgg tcaggataac acatgtgagg  1920
agtaccacac tgtgggccct cactcatgcc atatccccaa ggacctggcc ctcttcactc  1980
cctatgagat ctgggtggaa gccaccaatc gcctaggctc agcaagatct gatgtcctca  2040
cactggatgt cctggacgtg ggtgagcccc cagtgtccac ctgtgttctg ccctagacct  2100
tatagggcgc ctccccccca tccccccaga cttttttggtt cttctagagg tcttagccac  2160
agccacggtg gttgcaggac agtggttgtt cataacttaa tgcaaagact ttcccccaag  2220
acagtcaaga ttttttcccct ccccaccccc aacacacaca tacacacaca ctctgcagag  2280
aacacctggc ctgaccaccc tccctctcta cagcccaggt gttcagaagg gagtcctagg  2340
ggactgagag gaggcgccca ggtctgaagg cgccccagga agccgaggcc ttgagctggg  2400
gggggggcg agggttggag gcacgaactg gatgatccct gagcacaact gggcctaatc   2460
taattagggt gttcccagcc caaagcagcc tgggccattt aacccttcaa gtgcctcact  2520
gaagactcag gggagagatc agcttgtact ctctccatgg tcccccagga gggttcctgg  2580
gtgcccctgg ctcattccca catccagagg ttttgtgtct tcctggcatc taaccctcag  2640
ttgtgctctg tggctggcac agctgccccg tggaggctct tggtaatgta caaggcatca  2700
gaggtggaca tgggatgggg atacataggg atggagccaa atagcacctc aaggtgggt   2760
gatatacaat aaagcttgtc accctgacgc tcagaaagcc tactcatgat gatcacaatt  2820
gttgacatca ctctgggaca tgtagtgaga ccctagctca aaacacagac agtagcttta  2880
agagtcagct tgtgacttaa tactggaact caggggcctaa taggtgctgg gtgatgctcg  2940
cctcactccc tgtttagtga gatctctgcg ctaatctcca ccccagctgg gtgggctgct  3000
ctgtccccctt gagggcagga atgtgtgtct tccatcagag ataggacccg tggtagcagc  3060
aactgctgct ggctgtttct ggaatattaa atgacagtaa tctatcaggc ctgggtgagt  3120
```

```
agctaacagg ggtggggcg tggtctggaa aacgcagata gggtcatagg agccactgca    3180
gcctagatta caccactggg tgttctgtca ctaggccatt ctcaccaagc agtcctcaga    3240
actgggagca ctgttgccag catttaatgc cagcatttaa tgccagcatt aggggaggca    3300
gaggcagaag gatctctctg agttcaaggc catcctgaat ttacataaag agctccaggc    3360
cagccagggt gcgcagtaaa accttgtctc aaaaaacaaa gcatctttag tgaccaggct    3420
tgctccaccc ccagtgacca cggacccccc acccgacgtg cacgtgagcc gcgttggggg    3480
cctggaggac cagctgagtg tgcgctgggt ctcaccacca gctctcaagg atttcctctt    3540
ccaagccaag taccagatcc gctaccgcgt ggaggacagc gtggactgga aggtgcccgt    3600
cccgccccgg acccgcccct gaccccgccc ccgcatctg actcctccct caccgtgcag    3660
gtggtggatg acgtcagcaa ccagacctcc tgccgtctcg cgggcctgaa gcccggcacc    3720
gtttacttcg tccaagtgcg ttgtaaccca ttcgggatct atgggtcgaa aaaggcggga    3780
atctggagcg agtggagcca ccccaccgct gcctccaccc ctcgaagtgg tgagcacctc    3840
tccagggctg gctggcccat ggaatcccca atccatcctg ttccttcccc cccacccttt    3900
ttttgagaca gcgtcttcag gtagcgcatg ctggccttaa attcagtatg tagtcaagga    3960
tgacctcgag ctcctggtct ttttgtctcc acttagagac aatggccagt ggccatcacc    4020
acctttggga gactagccat ggagtctatt tagcctgtca tttggtgaca gatggagtac    4080
aacagtgtga cctcttgtaa gagaactgaa gacaggctgt ttttaacccc aatatcctag    4140
gctctctaga ggttaacttt atataaaata gagactatta cagccagtta tcacatggtc    4200
ccacagaacc ttttgtcaca caacctatag accacagtgc ctgtgcctac cacataaggg    4260
tctctactgc tggcccaccc ctccaaccct taaaaggtaa cctaggcagc cttaatattt    4320
gcaatcctcc tacctcagcc tcttgaatgc tcagaaacca ggcattaacc caagtttctc    4380
ttctctgggt ccctttctta aggtgggagg gcctaaagat gacttccttt gtcctgaaga    4440
ctctccgagc ccatggatct gcactctcta atatgaaata tattgcataa aatgtctggc    4500
ctcagtttcc ccacctgtca ggtttaggca gcacagtcgg tccaagacac ttcattattt    4560
gcaggcagta taagaagaag ctcccatccc ccacccgctt cctccggtcc ctaagacaga    4620
atacttctac actgaaactg aactctcgca gacgcatatg ctcactttaa tgatgatgaa    4680
ataatgggga aactgaggct ccgagagatt cctggaggaa gagggtcaaa accagctcca    4740
ggaagctctc cagcccccat ccgggcctct ccaggttctg ggcttggcgg gagtgaacac    4800
agctgggagg ggctggagcc tgggagcttt ggcccttgct cgtgcccagc acctgcgatt    4860
cttgcacggg agccagcagg cggctgcgtc cgcccgagag actgaagaag ccggggtag    4920 ggttggaggg aggtaagcag gggctgtggg ggccgaagct tgtgccaggg cctgtcagcg    4980
agtccccagt tttatttatg gcgtgaggcc gatgtcctta tccgctggcc tgctggggga    5040
tggctgcggc tggggattgg acccaagggc tggcttccca ctcagtcctc cagcccactc    5100
catgtcacac ccgtgcattc tctgaggctt atcttgggaa cccgcccttg ttctgtgctg    5160
tctgtctcta tttctgtcat tcactttccc agagcctttt ttttatgctt ttaatataac    5220
tacgttttaa aaattgcttt tgtataatgt gtgtgccttc gtgagcgtgc gtgccacaac    5280
acacacgtga aggttagaga actttgttga gtaggctcct tccaccatgt gggactaggg    5340
ctggcgacaa gagcaattac tgagtcatct cgccagcccc tcacccctca cttcccatcc    5400
tgtttggata gtcataggta atcgaaggta aatcgctggc tttaatttcg tagctatcct    5460
gcctcagcct accaagtgct gtgctaccac gtttgtggga ggggctctcc tcccagtgtc    5520
```

-continued

```
tggggtgac acagtcccaa gatctctgct ttctaggtct ttgtcttagt ttgccccttg      5580
ctttgtccgt gtccctagag tctccggccc cacttatcca ttgactggtc tttcctttac      5640
cgaatactcg gttttacctc ccactgattt gactccctcc tttgcttgtc tccatcgccg      5700
tggcattgcc attcctctgg gtgactctgg gtccacacct gaccctttc ccaactttcc      5760 ccagccgaag ctggtctggt atgggaggcc gccgtcccgc gcgcgcctcc tgctggccgc      5820
gccccaacac tgccgctcca ttctctttag agcgcccggg cccggcggc ggggtgtgcg       5880 agccgcgggg cggcgagccc agctcggccc cggtgcggcg cgagctcaag cagttcctcg      5940
gctggctcaa gaagcacgca tactgctcga accttagttt ccgcctgtac gaccagtggc      6000
gtgcttggat gcagaagtca cacaagaccc gaaaccaggt aggaaagttg ggggaggctt      6060
gcgtgggggg taaaggagca gaggaagaga gagacccggg tgagcagcct ccacaacacc      6120
gcactcttct ttccaagcac aggacgaggg gatcctgccc tcgggcagac ggggtgcggc      6180
gagaggtaag ggggtctggg tgagtggggc ctacagcagt ctagatgagg cccttttccc      6240
tccttcggtg ttgctcaaag ggatctctta gtgctcattt cacccactgc aaagagcccc      6300
aggttttact gcatcatcaa gttgctgaag gtccaggct taatgtggcc tcttttctgc       6360
cctcaggtcc tgccggctaa actctaagga taggccatcc tcctgctggg tcagacctgg      6420
aggctcacct gaattggagc ccctctgtac catctgggca acaaagaaac ctaccagagg      6480
ctgggcacaa tgagctccca caaccacagc tttggtccac atgatggtca cacttggata     6540 tacccccagtg tgggtagggt tggggtattg cagggcctcc caagagtctc tttaaataaa    6600
taaaggagtt gttcaggtcc cgatggccag tgtgtttggg gcctatgtgc tggggtgggg     6660
gga                                                                    6663
```

<210> SEQ ID NO 12
<211> LENGTH: 11832
<212> TYPE: DNA
<213> ORGANISM: Murine

<400> SEQUENCE: 12

```
gcggccgctg cagtgattac tcaccgcgtg gcgcacccca cccgcgggcc gctgagtgga      60 ttttttccgtg gggggatgtg aagaagttta gggagaactc ttctgcaccg atgggaacta    120
ggaatgcagg gttcggtccc gttccccaaa ggacacacct ctccccataa gcccactcat     180
aagggctccc tgcacgcgct ccgggacatc cccatatcca ataccccgcag atatgatagt    240 tgagaaggga ccagaggccg gagactccct ccctgccttc tggctttccc cccccctgc      300 acgaaacgag actacagcga tgggagaggt ggcatgaagg cttagggtgg ggatcggtag     360
gacccatgca cccagagaaa gggactggtg gcaactttca aactctctgg ggaaggaaga    420
agggctgaaa gaggatgaac gggctcaggt actgctcaat gtgtgtgtgg cggaccaaag    480
tgggtatggg ggccccgtaa gaggggcggg gaaggtggat aggaaggatc ccggtagact    540 ggagggggatc ctggaaaagc accagggctg cgagctagga acccattcgg agttaagggt   600
acaggatccc agatgagggg gtgggaagcc tgggacgggc gggaccagag agggaggtcc    660
cacgggctgg tggggaaaga gtgggggct tcgcgcagga ggatgggacg ttcaggagtg     720
gtaactgggc ggaggccggc cgggcgggc gcgcggtgcc cgcgggcggt gggaaggccg     780 gtgcgggcc cacgatcaac ccccccccag gggccggggcc gggccggggg cggggccggg    840
cggggcgagc ggcgcattag cgccttgtca atttcggctg ctcagacttg ctccggcctt    900
```

```
cgctgtccgc gcccagtgac gcgcgtgagg acccgagccc caatctgcac cccgcagact    960
cgcccccgcc ccataccggc gttgcagtca ccgcccgttg cgcgccaccc ccatgcccgc   1020
gggtcgcccg ggccccgtcg cccaatccgc gcggcggccg ccgcggccgc tgtcctcgct   1080
gtggtcgcct ctgttgctct gtgtcctcgg ggtgcctcgg ggcggatcgg gagcccgtga   1140
gtaccgtgcg ccctgctccc cacctcccca gggaagccgg gatccggcgc ccgggggggt   1200
agtcgcgggg gatggaagaa ggggcgcgag cgccacctgg acgtcccggg aacaaaggaa   1260
ggcggccctc ggggcgccct cacctgtggg gctcatggca ccaccaccca gcctcccaag   1320
agtaccccgt tatacatcag aggcctctta tctgtatccc ctttgcgagg ctgtctggcc   1380
aggctcagtt tgaaggacat cgcagtgtcc tgggaccccc ctccttcagg gtgctgggac   1440
gcttcggggc gcacgcctgt gtcttggata tcagagcgga agggaagcct ccctggccgg   1500
gggcgcacgc ttgggtgcgt tgggttgggt gctggcgcaa agtggggtcc cctcccccat   1560
gaagtgatga tccccggggg gagggtgggg cgttatcgtg agccctcctg tccgcctggc   1620
atgcggcccg gcgtccctcg ggacttgcct ctccgtgggg tcggcgccgc cccctccccc   1680
ctatagcaga ctccatgctt tggtatcctc gaagtcctct ccactggtgg ggctcacaac   1740
cggtctcatt caggctgcgc tgggttgaga gcctctagcg actgaaattt cggtgaggag   1800
cgagagcaag cgtgtccggg caccgcgagc ccagacttca ttgtctaagg gcacccagt   1860
gggggtcagc tgccgagaga atcccactgt cccaggagga actcctggcc ttgagccccc   1920
atcacccaac gcacacatcc ccgccaggat gcggtctcca catccagacc ctctctggga   1980
cacacccaaa gacacacaaa agagccccac tggcttatgt cccgtcaccc tgccctccga   2040
cgcgcgctgc agcccagatg cgtattcgca caccatcgcg gcgctcgcat tccatcctct   2100
acacacacac acacacacac acacacacac acacacacac acacacagac acgcacacac   2160
acacgcacgc acacacacgc acgcccgcac tcgtggtccc acatttattt cacaggggag   2220
gcaacaccgg ggtacgcata tggttgagtg cactggagat cttccccac cactctcagg    2280
accccatccg gagacacagg ccacaccgca ggggcaccac gctgcgctgc tgctctgggc   2340
tagtagtctt gtgcagtttg tccgcggtgt ctgtggacgc cctcccgctc ttgtcagggg   2400
acaggaacct acactcctgc ttgcccaagg cggctgggca ggtgatgtgg tgacacccgg   2460
gacctttccg gggagttggt gttgctgcca agcctgggta gtttttgaat gccaccaata   2520
gcgctaagct ttgtttccgg gcgggctgca gagcaacagg cgaaggtggc ggagtggggg   2580
tggcgcgtgt gttttttctt ttaaggggga gagaaattaa ataagaggtt ctcacacctc   2640
tgcaatctgt ttgtacttac cgtgtgtctt aacacctgac cagccagccg gtgggtcgta   2700
aaagtgtatg caggtaccag cgggacagga gatgggggcc cctggggtat ggctgggatg   2760
gaggccacct tcccgttggc ctttcaggga atctcacact tttcccttt aaaacacatg    2820
gtgttctttt taataacggc agcaactccg cattgggaaa gggggaaata agcttgtata   2880
ggccccggct ttgtggaaag gagggggaaga gggaagaaaa aaggagggagt gtctcctcca  2940
ggcttagggg gctgtcagct gctgctctgt ctagcttggc atgtgtgtgc cccagtcccc   3000
agtggctttg gccattgtt tgtggaagcc aagaggagagg ctggagtcct ctatctctgg   3060
tactccagag tcaggcttct cagtccgagc ccagagaacg tcttccctgt tttatggagg   3120
gaatcaggga aggggtgcc aggtggacta cgttctgctg aggactgtac cagtcgctcg    3180
aaggagaaag cttgggcttg cccccctccc ccctcaagcc acgaagggca gctgctaggc   3240
tagtgtggta aaagggcatt actccccagc caggaccccc cagagagtcc ccttcctggc   3300
```

```
                                                      -continued cagacaaatg ctggggaggg acagaggggt gtgatcattg cccaggagtg cagacagtgg    3360
ggtcccgggt cggcagtgc ctcccaccct gctgagggg gcgcccaggc aggaagcggt      3420
gggtgggccg gggtagagac gctggcacgt cccagttcat gccgaaggaa ttctgaatta    3480 gcggcggct ggctgcctgg gacctccggg gcggccccct ggccccgcc gctccgtctg      3540 gcctgctcct cctgctcctt cgcacggacg ctgagacctc cgctgagccc tgggacaagc    3600
cccaaatgca actgcgattg caggcttcgc aagacccgcc tcctcccaag gccaaatttg    3660
cctgggagaa gtcattcagg gcccagacta gaaccatgtt ggtgccacct catccatctg    3720
gggcatgaag gaccgtccag ggctgcagtt tagcttctta ataggaacct gggggtgggt    3780
gcagcctctg ttctccgagc ctctttggaa atcggttttg tttttgtttt tgttttttcc    3840
aatactcttt tcctctcatc ccatcccggg actgttttcc tccctaaggg ttgagagccc    3900
tgcagtcttc cctaaccttt tctttgcttc taccccaggg cctttgcaca tggagtccca    3960
cctctcccct tgcccaactg ggctccagc cttactgcat ttggctcttg gtaactgtcc     4020
cagggcctct ctgacacaca gggttgtagc cccagctccc tctcttctcc tccccccttt    4080
ctcttttgct tctgagactt aatttttttc ttttctttt tggcttttg agacagggtt      4140 tctctgtaca gccctggctg ccctggcact cattctgtag accaggctag cctcaaactc    4200
acaaacctac ctgcctctgc cttttccagtg ctggcactaa agatgtgggc caccacaact   4260
agtagttaag tgttttgctg tgtctttatt cctatagtga cctcagttcc tggcatattg    4320
taggcgatgg atggatgaat ggatggatgg atggatggat ggatggttgg atggagcaag    4380
cttgaatcgt cctgagtgaa aaagagacc tcagagaact gaatggagtt aggttcccag     4440
ggcagcctgg cctgctggtc tcatgggagc tccctgtgaa acttccccca cacctcccac    4500
caccctgcca tcctgtgtgg ctgacaagaa aggccaatgg ccagatgggg acacagactc    4560
agggaagctt ggaatatgtt cccctcctca tatcctaggc cttgttgtcc ccctgagggc    4620
ccagcctatg agtagggcag ctgtgggctg ccctaaggtt gggtaggcaa gaaggggtg     4680 gtccctcagg gtgggtcaca ggattgaggt catttccaaa gtggccatca cagtggccct    4740
aggaaatgat tgtggagagt cagaactcct gttgggagtt gtagagggcc ttgcatgtgg    4800
gcttctgtgg ctgtcccttc tcttgtggtc ctttgcacag tccctcgtg tgtgctggga    4860 tgtgaggagg gcacggggaa aatgaaggct cagcccctca gcttgcccctt cacggttcac   4920 ccaacagggc tcacctctcc tctggacagg ctctcactgt atgcacagat tggcctcaca    4980
tttgattccc ttcctttggt ctcctgggat gacaaacatt taccagggta ggattttaca    5040
ttttagatat gtccattctc cagaaacaca cttgtgaggt tagggtatca gtgaaaggac    5100
accaccagga cagacaaaga attggagagg aaggaaattg gtaagccagg ccatgcttga    5160
tggcttatgt gtaatcccag aactctggac gctgaggcag gaggattcca gtttcaaga    5220 cagtgtgttc taggtaatga gaccctgtca agaaagaaa agaaataaag agacaagaaa     5280
atgtttatag gctgtgagac agcttggtgg gtaaggggca cttgcctcca atcaagatga    5340
cctcagcccc atccctagga atccatggta gaaggagaaa gcaaactcca gctgctgacc    5400
tccatacatg tgctccaatg tgcacacaca caggagacaa taatcaatta ataggatgta    5460
tttgcttaga tttgagtagg catttatgac tgatgtttta aaatttttat ttgatttat    5520 gaaaatatac ctgtttgtat ttggtttggt ttggtttgag ttttgtttat ttgagacagg    5580
gcttctctgt gtagtcctgg ctgtccttgg aactcactct gtagaccagg ctggccttga    5640
```

```
actcagaaat ccgcctgctt gtgcttccca agtgcttaga ttaaaggtgt gcactgccat   5700
tcagcaaaat tgcatacttt aaccccagta tttgggaggc agaggcagac taatgtgtga   5760
attccaggct agccaaggat acagagtgag accctattct taccctcccc ccccaaaacc   5820
ccaaaatgta ttttgtgctt gtgtatgtac atgtgtgttg cagcacgtaa atgtccaagg   5880
acaacttgta gaagttctct ccgttcacag tctaagtcct gaattcaaac taaggtcctc   5940
aggcttagcc acagtcttct ttatgtactg agccatttca ctggccctgg attgactgat   6000
gaattaattt ttgagataag gtctcttgta gctctagcta ggctcaaact atgaactccc   6060
aaggtcatct tgagctgctg gtactcttgc ttccacccca agtggtggaa tgatactcag   6120
gcagcacttc tctggggaag gggctggcct tggccttgat tttgttgcct cagcttcaat   6180
gagtgcttgg gtctcgttgt ttcttttctt tatctgtgaa atgggtgaac acctgttcaa   6240
gacttcctga ctcttgaaac atccaggcag ggtgagggac ttgaagtggg ctcatcccat   6300
gcctaacaaa gtgtcgtctt tgaccccaga cacagctgta atcagccccc aggaccccac   6360
ccttctcatc ggctcctccc tgcaagctac ctgctctata catggagaca cacctggggc   6420
caccgctgag gggctctact ggaccttcaa tggtcgccgc ctgccctctg agctgtcccg   6480
cctccttaac acctccaccc tggccctggc cctggctaac cttaatgggt ccaggcagca   6540
gtcaggagac aatctggtgt gtcacgcccg agacggcagc attctggctg ctcctgcct   6600 ctatgttggc tgtaagtggg gccccagaca ctcagagata gatgggggtt ggcaatgaca   6660
gatttagagc ctgggtcttc tgtcctgggg cagagccatg ggctctcact tgcatgcagg   6720
catggtcata cccagcacag gcattgcaac tctagggaca gctgtggctg cactgtcccc   6780
tgtgtacccc acagctttag aaaagctgtc atgttttcct tgtagtgccc cctgagaagc   6840
cctttaacat cagctgctgg tcccggaaca tgaaggatct cacgtgccgc tggacaccgg   6900
gtgcacacgg ggagacattc ttacatacca actactccct caagtacaag ctgaggttgg   6960
tacccagcca agccttgctg tgtgacttct ggcaatactt accttctctg atcaaatatg   7020
ttcctgttta tgaactcaaa agggactctc gcacctccac aggtggtacg gtcaggataa   7080
cacatgtgag gagtaccaca ctgtgggccc tcactcatgc catatcccca aggacctggc   7140
cctcttcact ccctatgaga tctgggtgga agccaccaat cgcctaggct cagcaagatc   7200
tgatgtcctc acactggatg tcctggacgt gggtgagccc ccagtgtcca cctgtgttct   7260
gccctagacc ttatagggcg cctcccccccc atccccccag actttttggt tcttctagag   7320
gtcttagcca cagccacggt ggttgcagga cagtggttgt tcataactta atgcaaagac   7380
tttcccccaa gacagtcaag atttccccct ccccacccc aacacacaca tacacacaca   7440
ctctgcagag aacacctggc ctgaccaccc tccctctcta cagcccaggt gttcagaagg   7500
gagtcctagg ggactgagag gaggcgccca ggtctgaagg cgcccaggat agccgaggcc   7560
ttgagctggg gggggggggcg agggttggag gcacgaactg gatgatccct gagcacaact   7620
gggcctaatc taattagggt gttcccagcc caaagcagcc tgggccattt aacccttcaa   7680
gtgcctcact gaagactcag gggagagatc agcttgtact ctctccatgg tcccccagga   7740
gggttcctgg gtgcccctgg ctcattccca catccagagg ttttgtgtct tcctggcatc   7800
taaccctcag ttgtgctctg tggctggcac agctgccccg tggaggctct tggtaatgta   7860
caaggcatca gaggtggaca tgggatgggg atacataggg atggagccaa atagcacctc   7920
aaggtggggt gatatacaat aaagcttgtc accctgacgc tcagaaagcc tactcatgat   7980
gatcacaatt gttgacatca ctctgggaca tgtagtgaga ccctagctca aaacacagac   8040
```

-continued

```
agtagcttta agagtcagct tgtgacttaa tactggaact cagggcctaa taggtgctgg      8100
gtgatgctcg cctcactccc tgtttagtga gatctctgcg ctaatctcca ccccagctgg      8160
gtgggctgct ctgtcccctt gagggcagga atgtgtgtct tccatcagag ataggacccg      8220
tggtagcagc aactgctgct ggctgtttct ggaatattaa atgacagtaa tctatcaggc      8280
ctgggtgagt agctaacagg ggtgggggcg tggtctggaa aacgcagata gggtcatagg      8340
agccactgca gcctagatta caccactggg tgttctgtca ctaggccatt ctcaccaagc      8400
agtcctcaga actgggagca ctgttgccag catttaatgc cagcatttaa tgccagcatt      8460
aggggaggca gaggcagaag gatctctctg agttcaaggc catcctgaat ttacataaag      8520
agctccaggc cagccagggt gcgcagtaaa accttgtctc aaaaaacaaa gcatctttag      8580
tgaccaggct tgctccaccc ccagtgacca cggaccccccc acccgacgtg cacgtgagcc      8640
gcgttggggg cctggaggac cagctgagtg tgcgctgggt ctcaccacca gctctcaagg      8700
atttcctctt ccaagccaag taccagatcc gctaccgcgt ggaggacagc gtggactgga      8760
aggtgcccgt cccgcccccgg acccgcccct gaccccgccc ccgcatctg actcctccct      8820 caccgtgcag gtggtggatg acgtcagcaa ccagacctcc tgccgtctcg cgggcctgaa      8880
gcccggcacc gtttacttcg tccaagtgcg ttgtaaccca ttcgggatct atgggtcgaa      8940
aaaggcggga atctggagcg agtggagcca ccccaccgct gcctccaccc ctcgaagtgg      9000
tgagcacctc tccagggctg gctggcccat ggaatcccca atccatcctg ttccttcccc      9060
cccacccttt ttttgagaca gcgtcttcag gtagcgcatg ctggccttaa attcagtatg      9120
tagtcaagga tgacctcgag ctcctggtct ttttgtctcc acttagagac aatggccagt      9180
ggccatcacc acctttggga gactagccat ggagtctatt tagcctgtca tttggtgaca      9240
gatggagtac aacagtgtga cctcttgtaa gagaactgaa gacaggctgt ttttaacccc      9300
aatatcctag gctctctaga ggttaacttt atataaaata gagactatta cagccagtta      9360
tcacatggtc ccacagaacc ttttgtcaca caacctatag accacagtgc ctgtgcctac      9420
cacataaggg tctctactgc tggcccaccc ctccaacccct taaaaggtaa cctaggcagc      9480 cttaatatttt gcaatcctcc tacctcagcc tcttgaatgc tcagaaacca ggcattaacc      9540
caagtttctc ttctctgggt cccttttctta aggtgggagg gcctaaagat gacttccttt      9600
gtcctgaaga ctctccgagc ccatggatct gcactctcta atatgaaata tattgcataa      9660
aatgtctggc ctcagtttcc ccacctgtca ggtttaggca gcacagtcgg tccaagacac      9720 ttcattatttt gcaggcagta taagaagaag ctcccatccc ccacccgctt cctccggtcc      9780
ctaagacaga atacttctac actgaaactg aactctcgca gacgcatatg ctcactttaa      9840
tgatgatgaa ataatgggga aactgaggct ccgagagatt cctggaggaa gagggtcaaa      9900
accagctcca ggaagctctc cagcccccat ccgggcctct ccaggttctg gcttggcgg      9960 gagtgaacac agctgggagg ggctggagcc tgggagcttt ggcccttgct cgtgcccagc     10020
acctgcgatt cttgcacggg agccagcagg cggctgcgtc cgcccgagag actgaagaag     10080 ccggggtag ggttggaggg aggtaagcag gggctgtggg ggccgaagct tgtgccaggg     10140
cctgtcagcg agtccccagt tttatttatg gcgtgaggcc gatgtcctta tccgctggcc     10200
tgctggggga tggctgcggc tggggattgg acccaagggc tggcttccca ctcagtcctc     10260
cagcccactc catgtcacac ccgtgcattc tctgaggctt atcttgggaa cccgcccttg     10320
ttctgtgctg tctgtctcta tttctgtcat tcactttccc agagcctttt ttttatgctt     10380
```

-continued

```
ttaatataac tacgttttaa aaattgcttt tgtataatgt gtgtgccttc gtgagcgtgc    10440
gtgccacaac acacgtgaa aggttagaga actttgttga gtaggctcct tccaccatgt    10500
gggactaggg ctggcgacaa gagcaattac tgagtcatct cgccagcccc tcacccctca    10560
cttcccatcc tgtttggata gtcataggta atcgaaggta aatcgctggc tttaatttcg    10620
tagctatcct gcctcagcct accaagtgct gtgctaccac gtttgtggga ggggctctcc    10680
tcccagtgtc tgggggtaca cagtcccaag atctctgctt tctaggtctt tgtcttagtt    10740
tgccccttgc tttgtccgtg tccctagagt ctccggcccc acttagtctc cattgatttc    10800
ctttctgacc gaatactcgg ttttacctcc cactgatttg actccctcct ttgcttgtct    10860
ccatcgccgt ggcattgcca ttcctctggg tgactctggg tccacacctg acaccttttcc   10920 caactttccc cagccgaagc tggtctggta tgggaggccg ccgtcccgcg cgcgcctcct    10980
gctggccgcg ccccaacact gccgctccat tctctttaga gcgcccgggc ccgggcggcg    11040
gggtgtgcga gccgcgggc ggcgagccca gctcgggccc ggtgcggcgc gagctcaagc    11100
agttcctcgg ctggctcaag aagcacgcat actgctcgaa ccttagtttc cgcctgtacg    11160
accagtgggc tgcttggatg cagaagtcac acaagacccg aaaccaggta ggaaagttgg    11220
gggaggcttg cgtgggggt aaaggagcag aggaagagag agacccgggt gagcagcctc    11280
cacaacaccg cactcttctt tccaagcaca ggacgagggg atcctgccct cgggcagacg    11340
gggtgcggcg agaggtaagg gggtctgggt gagtggggcc tacagcagtc tagatgaggc    11400
cctttcccct ccttcggtgt tgctcaaagg gatctcttag tgctcatttc acccactgca    11460
aagagcccca ggttttactg catcatcaag ttgctgaagg gtccaggctt aatgtggcct    11520
cttttctgcc ctcaggtcct gccggctaaa ctctaaggat aggccatcct cctgctgggt    11580
cagacctgga ggctcacctg aattggagcc cctctgtacc atctgggcaa caaagaaacc    11640
taccagaggc tgggcacaat gagctcccac aaccacagct ttggtccaca tgatggtcac    11700
acttggatat accccagtgt gggtagggtt ggggtattgc agggcctccc aagagtctct    11760
ttaaataaat aaaggagttg ttcaggtccc gatggccagt gtgtttgggg cctatgtgct    11820
ggggtggggg ga                                                       11832
```

<210> SEQ ID NO 13
<211> LENGTH: 2079
<212> TYPE: DNA
<213> ORGANISM: Murine
<220> FEATURE:
<221> NAME/KEY: CDS
<222> LOCATION: (513)..(1778)

<400> SEQUENCE: 13

```
gcggtatttg tgtttcaaat ctatctacag aaaagattga gaaccagaag ccctttttcgt    60 tttttgaaag ctagctgact cactgttcaa gaaaggagaa cactttcaat tatgctgttt   120
gactgcagtg tcagggatcc aaaggaaatg actccatccc ttcccttttca tcccaacctc   180 agtgacagca aattctgatg tgactgaggg ttggcttgtg aaggagtcat taggaaattc   240
tgcctaagcc atagcgcgat gagaaggatg tatcctatgg tggtgatttt cctgtgcccc   300
ctcagaggaa agttgtcaga tgagcaggtg gagtattcta tagcaaacag caagctaata   360
ggttacacag ataactctct gactttgcct tacagaacct gtgctattga ccttagggca   420
aggttcatgc tcaggggcc aactctgtgg gttaggattt gagtttaagc agcttctgct   480
catatttcag cgcccccggc agcgccggcc cc atg ccc gcc ggc cgc cgg ggc      533
                                  Met Pro Ala Gly Arg Arg Gly
```

-continued

```
                            1                   5
ccc gcc gcc caa tcc gcg cgg cgg ccg ccg ttg ctg ccc ctg ctg        581
Pro Ala Ala Gln Ser Ala Arg Arg Pro Pro Leu Leu Pro Leu Leu
            10                  15                  20 ctg ctc tgc gtc ctc ggg gcg ccg cga gcc gga tca gga gcc cac aca    629
Leu Leu Cys Val Leu Gly Ala Pro Arg Ala Gly Ser Gly Ala His Thr
        25                  30                  35 gct gtg atc agt ccc cag gat ccc acg ctt ctc atc ggc tcc tcc ctg    677
Ala Val Ile Ser Pro Gln Asp Pro Thr Leu Leu Ile Gly Ser Ser Leu
40                  45                  50                  55 ctg gcc acc tgc tca gtg cac gga gac cca cca gga gcc acc gcc gag    725
Leu Ala Thr Cys Ser Val His Gly Asp Pro Pro Gly Ala Thr Ala Glu
                60                  65                  70 ggc ctc tac tgg acc ctc aat ggg cgc cgc ctg ccc cct gag ctc tcc    773
Gly Leu Tyr Trp Thr Leu Asn Gly Arg Arg Leu Pro Pro Glu Leu Ser
            75                  80                  85 cgt gta ctc aac gcc tcc acc ttg gct ctg gcc ctg gcc aac ctc aat    821
Arg Val Leu Asn Ala Ser Thr Leu Ala Leu Ala Leu Ala Asn Leu Asn
        90                  95                  100 ggg tcc agg cag cgg tcg ggg gac aac ctc gtg tgc cac gcc cgt gac    869
Gly Ser Arg Gln Arg Ser Gly Asp Asn Leu Val Cys His Ala Arg Asp
    105                 110                 115 ggc agc atc ctg gct ggc tcc tgc ctc tat gtt ggc ctg ccc cca gag    917
Gly Ser Ile Leu Ala Gly Ser Cys Leu Tyr Val Gly Leu Pro Pro Glu
120                 125                 130                 135 aaa ccc gtc aac atc agc tgc tgg tcc aag aac atg aag gac ttg acc    965
Lys Pro Val Asn Ile Ser Cys Trp Ser Lys Asn Met Lys Asp Leu Thr
            140                 145                 150 tgc cgc tgg acg cca ggg gcc cac ggg gag acc ttc ctc cac acc aac    1013
Cys Arg Trp Thr Pro Gly Ala His Gly Glu Thr Phe Leu His Thr Asn
        155                 160                 165 tac tcc ctc aag tac aag ctt agg tgg tat ggc cag gac aac aca tgt    1061
Tyr Ser Leu Lys Tyr Lys Leu Arg Trp Tyr Gly Gln Asp Asn Thr Cys
    170                 175                 180 gag gag tac cac aca gtg ggg ccc cac tcc tgc cac atc ccc aag gac    1109
Glu Glu Tyr His Thr Val Gly Pro His Ser Cys His Ile Pro Lys Asp
185                 190                 195 ctg gct ctc ttt acg ccc tat gag atc tgg gtg gag gcc acc aac cgc    1157
Leu Ala Leu Phe Thr Pro Tyr Glu Ile Trp Val Glu Ala Thr Asn Arg
200                 205                 210                 215 ctg ggc tct gcc cgc tcc gat gta ctc acg ctg gat atc ctg gat gtg    1205
Leu Gly Ser Ala Arg Ser Asp Val Leu Thr Leu Asp Ile Leu Asp Val
            220                 225                 230 gtg acc acg gac ccc ccg ccc gac gtg cac gtg agc cgc gtc ggg ggc    1253
Val Thr Thr Asp Pro Pro Pro Asp Val His Val Ser Arg Val Gly Gly
        235                 240                 245 ctg gag gac cag ctg agc gtg cgc tgg gtg tcg cca ccc gcc ctc aag    1301
Leu Glu Asp Gln Leu Ser Val Arg Trp Val Ser Pro Pro Ala Leu Lys
    250                 255                 260 gat ttc ctc ttt caa gcc aaa tac cag atc cgc tac cga gtg gag gac    1349
Asp Phe Leu Phe Gln Ala Lys Tyr Gln Ile Arg Tyr Arg Val Glu Asp
265                 270                 275 agt gtg gac tgg aag gtg gtg gac gat gtg agc aac cag acc tcc tgc    1397
Ser Val Asp Trp Lys Val Val Asp Asp Val Ser Asn Gln Thr Ser Cys
280                 285                 290                 295 cgc ctg gcc ggc ctg aaa ccc ggc acc gtg tac ttc gtg caa gtg cgc    1445
Arg Leu Ala Gly Leu Lys Pro Gly Thr Val Tyr Phe Val Gln Val Arg
            300                 305                 310 tgc aac ccc ttt ggc atc tat ggc tcc aag aaa gcc ggg atc tgg agt    1493
Cys Asn Pro Phe Gly Ile Tyr Gly Ser Lys Lys Ala Gly Ile Trp Ser
```

```
                Cys Asn Pro Phe Gly Ile Tyr Gly Ser Lys Lys Ala Gly Ile Trp Ser
                                315                 320                 325 gag tgg agc cac ccc aca gcc gcc tcc act ccc cgc agt gag cgc ccg            1541
Glu Trp Ser His Pro Thr Ala Ala Ser Thr Pro Arg Ser Glu Arg Pro
            330                 335                 340 ggc ccg ggc ggc ggg gcg tgc gaa ccg cgg ggc gga gag ccg agc tcg            1589
Gly Pro Gly Gly Gly Ala Cys Glu Pro Arg Gly Gly Glu Pro Ser Ser
345                 350                 355 ggg ccg gtg cgg cgc gag ctc aag cag ttc ctg ggc tgg ctc aag aag            1637
Gly Pro Val Arg Arg Glu Leu Lys Gln Phe Leu Gly Trp Leu Lys Lys
360                 365                 370                 375 cac gcg tac tgc tcc aac ctc agc ttc cgc ctc tac gac cag tgg cga            1685
His Ala Tyr Cys Ser Asn Leu Ser Phe Arg Leu Tyr Asp Gln Trp Arg
                380                 385                 390 gcc tgg atg cag aag tcg cac aag acc cgc aac cag gac gag ggg atc            1733
Ala Trp Met Gln Lys Ser His Lys Thr Arg Asn Gln Asp Glu Gly Ile
            395                 400                 405 ctg ccc tcg ggc aga cgg ggc acg gcg aga ggt cct gcc aga taa                1778
Leu Pro Ser Gly Arg Arg Gly Thr Ala Arg Gly Pro Ala Arg
            410                 415                 420 gctgtagggg ctcaggccac cctccctgcc acgtggagac gcagaggccg aacccaaact          1838
ggggccacct ctgtaccctc acttcagggc acctgagcca ccctcagcag gagctggggt          1898 ggccccctgag ctccaacggc cataacagct ctgactccca cgtgaggcca cctttgggtg         1958 cacccccagtg ggtgtgtgtg tgtgtgtgag ggttggttga gttgcctaga accccctgcca        2018 gggctggggg tgagaagggg agtcattact ccccattacc tagggcccct ccaaaagatc          2078
c                                                                          2079

<210> SEQ ID NO 14
<211> LENGTH: 421
<212> TYPE: PRT
<213> ORGANISM: Murine

<400> SEQUENCE: 14

Met Pro Ala Gly Arg Gly Pro Ala Ala Gln Ser Ala Arg Arg Pro
1               5                   10                  15

Pro Pro Leu Leu Pro Leu Leu Leu Cys Val Leu Gly Ala Pro Arg
                20                  25                  30

Ala Gly Ser Gly Ala His Thr Ala Val Ile Ser Pro Gln Asp Pro Thr
            35                  40                  45

Leu Leu Ile Gly Ser Ser Leu Ala Thr Cys Ser Val His Gly Asp
    50                  55                  60

Pro Pro Gly Ala Thr Ala Glu Gly Leu Tyr Trp Thr Leu Asn Gly Arg
65                  70                  75                  80

Arg Leu Pro Pro Glu Leu Ser Arg Val Leu Asn Ala Ser Thr Leu Ala
                85                  90                  95

Leu Ala Leu Ala Asn Leu Asn Gly Ser Arg Gln Arg Ser Gly Asp Asn
                100                 105                 110

Leu Val Cys His Ala Arg Asp Gly Ser Ile Leu Ala Gly Ser Cys Leu
            115                 120                 125

Tyr Val Gly Leu Pro Pro Glu Lys Pro Val Asn Ile Ser Cys Trp Ser
    130                 135                 140

Lys Asn Met Lys Asp Leu Thr Cys Arg Trp Thr Pro Gly Ala His Gly
145                 150                 155                 160

Glu Thr Phe Leu His Thr Asn Tyr Ser Leu Lys Tyr Lys Leu Arg Trp
                165                 170                 175
```

-continued

```
Tyr Gly Gln Asp Asn Thr Cys Glu Glu Tyr His Thr Val Gly Pro His
            180                 185                 190

Ser Cys His Ile Pro Lys Asp Leu Ala Leu Phe Thr Pro Tyr Glu Ile
        195                 200                 205

Trp Val Glu Ala Thr Asn Arg Leu Gly Ser Ala Arg Ser Asp Val Leu
    210                 215                 220

Thr Leu Asp Ile Leu Asp Val Val Thr Thr Asp Pro Pro Asp Val
225                 230                 235                 240

His Val Ser Arg Val Gly Gly Leu Glu Asp Gln Leu Ser Val Arg Trp
                245                 250                 255

Val Ser Pro Pro Ala Leu Lys Asp Phe Leu Phe Gln Ala Lys Tyr Gln
            260                 265                 270

Ile Arg Tyr Arg Val Glu Asp Ser Val Asp Trp Lys Val Asp Asp
        275                 280                 285

Val Ser Asn Gln Thr Ser Cys Arg Leu Ala Gly Leu Lys Pro Gly Thr
    290                 295                 300

Val Tyr Phe Val Gln Val Arg Cys Asn Pro Phe Gly Ile Tyr Gly Ser
305                 310                 315                 320

Lys Lys Ala Gly Ile Trp Ser Glu Trp Ser His Pro Thr Ala Ala Ser
                325                 330                 335

Thr Pro Arg Ser Glu Arg Pro Gly Pro Gly Gly Ala Cys Glu Pro
            340                 345                 350

Arg Gly Gly Glu Pro Ser Ser Gly Pro Val Arg Arg Glu Leu Lys Gln
        355                 360                 365

Phe Leu Gly Trp Leu Lys Lys His Ala Tyr Cys Ser Asn Leu Ser Phe
    370                 375                 380

Arg Leu Tyr Asp Gln Trp Arg Ala Trp Met Gln Lys Ser His Lys Thr
385                 390                 395                 400

Arg Asn Gln Asp Glu Gly Ile Leu Pro Ser Gly Arg Arg Gly Thr Ala
                405                 410                 415

Arg Gly Pro Ala Arg
            420

<210> SEQ ID NO 15
<211> LENGTH: 182
<212> TYPE: PRT
<213> ORGANISM: Murine

<400> SEQUENCE: 15

Asp Pro Thr Leu Leu Ile Gly Ser Ser Leu Gln Ala Thr Cys Ser Ile
1               5                   10                  15

His Gly Asp Thr Pro Gly Ala Thr Ala Glu Gly Leu Tyr Trp Thr Phe
            20                  25                  30

Asn Gly Arg Arg Leu Pro Ser Glu Leu Ser Arg Leu Leu Asn Thr Ser
        35                  40                  45

Thr Leu Ala Leu Ala Leu Ala Asn Leu Asn Gly Ser Arg Gln Gln Ser
    50                  55                  60

Gly Asp Asn Leu Val Cys His Ala Arg Asp Gly Ser Ile Leu Ala Gly
65                  70                  75                  80

Ser Cys Leu Tyr Val Gly Leu Pro Pro Glu Lys Pro Phe Asn Ile Ser
                85                  90                  95

Cys Trp Ser Arg Asn Met Lys Asp Leu Thr Cys Arg Trp Thr Pro Gly
            100                 105                 110

Ala His Gly Glu Thr Phe Leu His Thr Asn Tyr Ser Leu Lys Tyr Lys
```

```
                115                 120                 125
Leu Arg Leu Val Arg Ser Gly His Met Gly Val Pro His Cys Gly Pro
    130                 135                 140

Ser Leu Met Pro Tyr Pro Gln Gly Pro Gly Pro Leu His Ser Leu Asp
145                 150                 155                 160

Leu Gly Gly Ser His Gln Ser Pro Arg Leu Ser Lys Ile Cys Pro His
                165                 170                 175

Thr Gly Cys Pro Gly Arg
            180

<210> SEQ ID NO 16
<211> LENGTH: 421
<212> TYPE: PRT
<213> ORGANISM: Murine

<400> SEQUENCE: 16

Met Pro Ala Gly Arg Arg Gly Pro Ala Ala Gln Ser Ala Arg Arg Pro
1               5                   10                  15

Pro Pro Leu Leu Pro Leu Leu Leu Cys Val Leu Gly Ala Pro Arg
            20                  25                  30

Ala Gly Ser Gly Ala His Thr Ala Val Ile Ser Pro Gln Asp Pro Thr
            35                  40                  45

Leu Leu Ile Gly Ser Ser Leu Leu Ala Thr Cys Ser Val His Gly Asp
    50                  55                  60

Pro Pro Gly Ala Thr Ala Glu Gly Leu Tyr Trp Thr Leu Asn Gly Arg
65                  70                  75                  80

Arg Leu Pro Pro Glu Leu Ser Arg Val Leu Asn Ala Ser Thr Leu Ala
                85                  90                  95

Leu Ala Leu Ala Asn Leu Asn Gly Ser Arg Gln Arg Ser Gly Asp Asn
            100                 105                 110

Leu Val Cys His Ala Arg Asp Gly Ser Ile Leu Ala Gly Ser Cys Leu
            115                 120                 125

Tyr Val Gly Leu Pro Pro Glu Lys Pro Val Asn Ile Ser Cys Trp Ser
    130                 135                 140

Lys Asn Met Lys Asp Leu Thr Cys Arg Trp Thr Pro Gly Ala His Gly
145                 150                 155                 160

Glu Thr Phe Leu His Thr Asn Tyr Ser Leu Lys Tyr Lys Leu Arg Trp
                165                 170                 175

Tyr Gly Gln Asp Asn Thr Cys Glu Glu Tyr His Thr Val Gly Pro His
            180                 185                 190

Ser Cys His Ile Pro Lys Asp Leu Ala Leu Phe Thr Pro Tyr Glu Ile
            195                 200                 205

Trp Val Glu Ala Thr Asn Arg Leu Gly Ser Ala Arg Ser Asp Val Leu
    210                 215                 220

Thr Leu Asp Ile Leu Asp Val Val Thr Thr Asp Pro Pro Asp Val
225                 230                 235                 240

His Val Ser Arg Val Gly Gly Leu Glu Asp Gln Leu Ser Val Arg Trp
                245                 250                 255

Val Ser Pro Pro Ala Leu Lys Asp Phe Leu Phe Gln Ala Lys Tyr Gln
            260                 265                 270

Ile Arg Tyr Arg Val Glu Asp Ser Val Asp Trp Lys Val Val Asp Asp
            275                 280                 285

Val Ser Asn Gln Thr Ser Cys Arg Leu Ala Gly Leu Lys Pro Gly Thr
    290                 295                 300
```

-continued

```
Val Tyr Phe Val Gln Val Arg Cys Asn Pro Phe Gly Ile Tyr Gly Ser
305                 310                 315                 320

Lys Lys Ala Gly Ile Trp Ser Glu Trp Ser His Pro Thr Ala Ala Ser
            325                 330                 335

Thr Pro Arg Ser Glu Arg Pro Gly Pro Gly Gly Ala Cys Glu Pro
        340                 345                 350

Arg Gly Gly Glu Pro Ser Ser Gly Pro Val Arg Arg Glu Leu Lys Gln
            355                 360                 365

Phe Leu Gly Trp Leu Lys Lys His Ala Tyr Cys Ser Asn Leu Ser Phe
        370                 375                 380

Arg Leu Tyr Asp Gln Trp Arg Ala Trp Met Gln Lys Ser His Lys Thr
385                 390                 395                 400

Arg Asn Gln Asp Glu Gly Ile Leu Pro Ser Gly Arg Arg Gly Thr Ala
                405                 410                 415

Arg Gly Pro Ala Arg
            420
```

<210> SEQ ID NO 17
<211> LENGTH: 143
<212> TYPE: DNA
<213> ORGANISM: Artificial Sequence
<220> FEATURE:
<223> OTHER INFORMATION: Description of Artificial Sequence:Nucleotide
      sequence unique to 5' RACE of brain cDNA
<220> FEATURE:
<221> NAME/KEY: CDS
<222> LOCATION: (105)..(143)

<400> SEQUENCE: 17

```
ggcatgaagg cttagggtgg ggatcggtag gacccatgca cccagagaaa gggactggtg      60
gcaactttca aactctctgg ggaaggaaga agggctgaaa gagg atg aac ggg ctc      116
                                                Met Asn Gly Leu
                                                  1 aga cac agc tgt aat cag ccc cca gga                                   143
Arg His Ser Cys Asn Gln Pro Pro Gly
  5                  10
```

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence:Peptide
      sequence encoded by the nucleotide sequences as set forth in
      SEQ ID NO: 17

<400> SEQUENCE: 18

```
Met Asn Gly Leu Arg His Ser Cys Asn Gln Pro Pro Gly
  1               5                   10
```

<210> SEQ ID NO 19
<211> LENGTH: 729
<212> TYPE: DNA
<213> ORGANISM: human
<220> FEATURE:
<221> NAME/KEY: CDS
<222> LOCATION: (11)..(679)

<400> SEQUENCE: 19

```
cgaattcccc atg gac ctc cga gca ggg gac tcg tgg ggg atg tta gcg      49
           Met Asp Leu Arg Ala Gly Asp Ser Trp Gly Met Leu Ala
             1               5                  10 tgc ctg tgc acg gtg ctc tgg cac ctc cct gca gtg cca gct ctc aat    97
```

-continued

| | | | | | | | | | | | | | | |
|---|---|---|---|---|---|---|---|---|---|---|---|---|---|---|
| Cys | Leu | Cys | Thr | Val | Leu | Trp | His | Leu | Pro | Ala | Val | Pro | Ala | Leu | Asn |
| | 15 | | | | 20 | | | | 25 | | | | | |

```
cgc aca ggg gac cca ggg cct ggc ccc tcc atc cag aaa acc tat gac    145
Arg Thr Gly Asp Pro Gly Pro Gly Pro Ser Ile Gln Lys Thr Tyr Asp
 30              35                  40                  45 ctc acc cgc tac ctg gag cac caa ctc cgc agc ttg gct ggg acc tat    193
Leu Thr Arg Tyr Leu Glu His Gln Leu Arg Ser Leu Ala Gly Thr Tyr
                 50                  55                  60 ctg aac tac ctg ggc ccc cct ttc aac gag cca gac ttc aac cct ccc    241
Leu Asn Tyr Leu Gly Pro Pro Phe Asn Glu Pro Asp Phe Asn Pro Pro
                65                  70                  75 cgc ctg ggg gca gag act ctg ccc agg gcc act gtt gac ttg gag gtg    289
Arg Leu Gly Ala Glu Thr Leu Pro Arg Ala Thr Val Asp Leu Glu Val
             80                  85                  90 tgg cga agc ctc aat gac aaa ctg cgg ctg acc cag aac tac gag gcc    337
Trp Arg Ser Leu Asn Asp Lys Leu Arg Leu Thr Gln Asn Tyr Glu Ala
         95                 100                 105 tac agc cac ctt ctg tgt tac ttg cgt ggc ctc aac cgt cag gct gcc    385
Tyr Ser His Leu Leu Cys Tyr Leu Arg Gly Leu Asn Arg Gln Ala Ala
110             115                 120                 125 act gct gag ctg cgc cgc agc ctg gcc cac ttc tgc acc agc ctc cag    433
Thr Ala Glu Leu Arg Arg Ser Leu Ala His Phe Cys Thr Ser Leu Gln
                130                 135                 140 ggc ctg ctg ggc agc att gcg ggc gtc atg gca gct ctg ggc tac cca    481
Gly Leu Leu Gly Ser Ile Ala Gly Val Met Ala Ala Leu Gly Tyr Pro
                    145                 150                 155 ctg ccc cag ccg ctg cct ggg act gaa ccc act tgg act cct ggc cct    529
Leu Pro Gln Pro Leu Pro Gly Thr Glu Pro Thr Trp Thr Pro Gly Pro
            160                 165                 170 gcc cac agt gac ttc ctc cag aag atg gac gac ttc tgg ctg ctg aag    577
Ala His Ser Asp Phe Leu Gln Lys Met Asp Asp Phe Trp Leu Leu Lys
        175                 180                 185 gag ctg cag acc tgg ctg tgg cgc tcg gcc aag gac ttc aac cgg ctc    625
Glu Leu Gln Thr Trp Leu Trp Arg Ser Ala Lys Asp Phe Asn Arg Leu
190                 195                 200                 205 aag aag aag atg cag cct cca gca gct gca gtc acc ctg cac ctg ggg    673
Lys Lys Lys Met Gln Pro Pro Ala Ala Ala Val Thr Leu His Leu Gly
                210                 215                 220 gct cat ggcttctgac ttctgacctt ctcctcttcg ctccccttc aaggatccc       729
Ala His
```

<210> SEQ ID NO 20
<211> LENGTH: 223
<212> TYPE: PRT
<213> ORGANISM: human

<400> SEQUENCE: 20

```
Met Asp Leu Arg Ala Gly Asp Ser Trp Gly Met Leu Ala Cys Leu Cys
 1               5                  10                  15

Thr Val Leu Trp His Leu Pro Ala Val Pro Ala Leu Asn Arg Thr Gly
                 20                  25                  30

Asp Pro Gly Pro Gly Pro Ser Ile Gln Lys Thr Tyr Asp Leu Thr Arg
             35                  40                  45

Tyr Leu Glu His Gln Leu Arg Ser Leu Ala Gly Thr Tyr Leu Asn Tyr
         50                  55                  60

Leu Gly Pro Pro Phe Asn Glu Pro Asp Phe Asn Pro Pro Arg Leu Gly
 65                  70                  75                  80

Ala Glu Thr Leu Pro Arg Ala Thr Val Asp Leu Glu Val Trp Arg Ser
                 85                  90                  95
```

-continued

Leu Asn Asp Lys Leu Arg Leu Thr Gln Asn Tyr Glu Ala Tyr Ser His
            100                 105                 110

Leu Leu Cys Tyr Leu Arg Gly Leu Asn Arg Gln Ala Ala Thr Ala Glu
        115                 120                 125

Leu Arg Arg Ser Leu Ala His Phe Cys Thr Ser Leu Gln Gly Leu Leu
    130                 135                 140

Gly Ser Ile Ala Gly Val Met Ala Ala Leu Gly Tyr Pro Leu Pro Gln
145                 150                 155                 160

Pro Leu Pro Gly Thr Glu Pro Thr Trp Thr Pro Gly Pro Ala His Ser
                165                 170                 175

Asp Phe Leu Gln Lys Met Asp Asp Phe Trp Leu Leu Lys Glu Leu Gln
            180                 185                 190

Thr Trp Leu Trp Arg Ser Ala Lys Asp Phe Asn Arg Leu Lys Lys Lys
        195                 200                 205

Met Gln Pro Pro Ala Ala Ala Val Thr Leu His Leu Gly Ala His
    210                 215                 220

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:sense primer

<400> SEQUENCE: 21
cgaattcccc atggacctcc gagcag                                    26

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:antisense
      primer

<400> SEQUENCE: 22
gggatccttt gaagggggag cgaagag                                   27

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:HA epitope
      tag

<400> SEQUENCE: 23

Tyr Pro Tyr Asp Val Pro Asp Tyr Ala Ser
1               5                   10

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence:IL-3 signal
      sequence

<400> SEQUENCE: 24

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser

-continued

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:sense primer

<400> SEQUENCE: 25
ccatttcagg tgtcgtgagg                                                  20

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence:antisense
      primer

<400> SEQUENCE: 26
gtagtcgggc acgtcataag gatacgagat tgaagcttgg agtcc                      45

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence:sense primer

<400> SEQUENCE: 27
ccttatgacg tgcccgacta cgccagtctc aatcgcacag gggaccca                   48

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:the
      N-terminal sequence of the 27-29 KD protein
<220> FEATURE:
<221> NAME/KEY: Unsure
<222> LOCATION: (2)
<223> OTHER INFORMATION: Xaa can be any amino acid

<400> SEQUENCE: 28

Leu Xaa Arg Thr Gly Asp Pro Gly Pro Gly Pro Ser Ile
 1               5                  10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence:the
      N-terminal sequence of CLC

<400> SEQUENCE: 29

Leu Asn Arg Thr Gly Asp Pro Gly Pro Gly Pro Ser Ile
 1               5                  10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence:artificial
      peptide

```
<400> SEQUENCE: 30

Ala Ser Ile Ser Ala Arg Gln Asp Tyr Lys Asp Asp Asp Asp
 1               5                  10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:artificial
      peptide
<220> FEATURE:
<221> NAME/KEY: Unsure
<222> LOCATION: (2)
<223> OTHER INFORMATION: Xaa can be any amino acid

<400> SEQUENCE: 31

Leu Xaa Arg Thr Gly Asp Pro Gly Pro Ser Ile Gln Lys
 1               5                  10
```